US006949337B2

(12) United States Patent
Weiner et al.

(10) Patent No.: US 6,949,337 B2
(45) Date of Patent: Sep. 27, 2005

(54) CELLULAR RECEPTOR FOR HIV-1 VPR ESSENTIAL FOR G2/M PHASE TRANSITION OF THE CELL CYCLE

(75) Inventors: David B. Weiner, Merion Station, PA (US); Velpandi Ayyavoo, Monroeville, PA (US); Sundarasamy Mahalingam, Birmingham, AL (US); Mamata Patel, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 10/208,338

(22) Filed: Jul. 29, 2002

(65) Prior Publication Data

US 2003/0143735 A1 Jul. 31, 2003

Related U.S. Application Data

(63) Continuation of application No. 09/529,245, filed as application No. PCT/US98/21432 on Oct. 9, 1998, now Pat. No. 6,448,078, which is a continuation of application No. 08/949,202, filed on Oct. 10, 1997, now Pat. No. 6,060,587.

(51) Int. Cl.$^7$ .......................... C12Q 1/70; C12Q 1/68; C12P 21/06; A61K 38/00; G01N 33/00
(52) U.S. Cl. .......................... 435/5; 435/6; 435/69.1; 435/172.3; 435/339.1; 435/974; 530/300; 530/350; 800/3; 800/18; 800/25
(58) Field of Search .......................... 435/5, 6, 69.1, 435/172.3, 339.1, 974; 530/300, 350; 800/3, 18, 25

(56) References Cited

U.S. PATENT DOCUMENTS

| 4,736,866 A | 4/1988 | Leder et al. |
|---|---|---|
| 4,873,191 A | 10/1989 | Wagner et al. |
| 5,001,230 A | 3/1991 | Brown et al. |
| 5,108,921 A | 4/1992 | Low et al. |
| 6,060,587 A | * 5/2000 | Weiner et al. ............ 530/350 |
| 6,448,078 B1 | * 9/2002 | Weiner et al. ............ 435/339.1 |

OTHER PUBLICATIONS

Adachi, et al., "Production of Acquired Immunodeficiency Syndrome: Associated Retrovirus un Human and Nonhuman Cells Transfected with an Infectious Molecular Clone," J. Virol. (1986) 59:284–291.

Aguanno, et al., "12–O–Tetradecanoylphorbol–13–Acetate–induced Differentiation of a Human Rhabdomyosarcoma Cell Line," Cencer Res. (1990)50:3377–3382.

Arya, et al., "Trans–Activator Gene of Human T–Lymphocyte Virus Type III (HTLV–III)," Science (1985) 229–69–73.

Balliet, et al., "Distinct Effects in Primary Macrophages and Lymphocytes of the Human Immunodeficiency Virus Type I Accessory Genes vpr, vpu, and nef: Mutational Analysis of a Primary HIV–I Isolate," Virology (1994)200:623–631.

(Continued)

*Primary Examiner*—Hankyel T. Park
(74) *Attorney, Agent, or Firm*—Cozen O'Connor, P.C.

(57) ABSTRACT

The present invention provides methods of identifying anti-HIV compound by contacting human Vpr Interacting Protein (hVIP), or a fragment thereof known to interact with Vpr, with Vpr, or a fragment thereof known to interact with hVIP in the presence of a test compound, and comparing the affinity of the hVIP or fragment thereof to the Vpr or fragment thereof in the presence of the test compound with the affinity of the hVIP or fragment thereof to the Vpr or fragment thereof in the absence of the test compound. The present invention also provides transgenic non-human mammals comprising a recombinant expression vector that comprises a nucleic acid sequence that encodes hVIP.

28 Claims, 10 Drawing Sheets

```
1    M H A R A A A S V M D I C R I R L D H A V S M S T    25
26   F F F F L S S G M E V D A A V V P S V M A C G V T    50
51   G S V S V A L H P L V I L N I S D H W I R M R S H    75
76   Q G R P V Q V I G A L I G K Q E G R N I E V M N S    100
101  F E L L S H T V E E K I I I D K E Y Y Y T K E E Q    125
126  F K Q V F K E L E F L G W Y T T G G P P D P S D I    150
151  H V H K Q C C E I I E S P L F L K L N P M T K H T    175
176  D L P V S V F E S V I D I I N G E A T M L F A E L    200
201  T Y T L A T E E A E R I G V D H V A R M T A T G S    225
226  G E N S T V A E H L I A Q H S A I K M L H S R V K    250
251  L I L E Y V K A S E A G E V P F N H E I L R E A Y    275
276  A L C H C L P V L S T D K F K T D F Y D Q C N D V    300
301  G L M A Y L G T I T K T C N T M N Q F V N K F N V    325
326  L Y D R Q G I G R R M R G L F F *                    341
```

OTHER PUBLICATIONS

Balotta, et al., "Antisense Phosphorothioate Oligodeoxynucleotides Targeted to the vpr GeneInhibit Immunodeficiency Virus Type I Replication in Primary Human Macrophages," J. Virol. (1993) 67:4409–4414.

Chantal Petit, et al., "Human Immunodeficiency VirusInfection Down–Regulates HLA Class II Expression and Induces Differentiation inPromonocytic U937 Cells," J. Clin Invest. (1987) 79:1883–1889.

Cohen, et al., "Human Immunodeficiency Virus vpr Product is a Viron–Associated Regulatory Protein," J. Virol. (1990) 64:3097–3099.

Cohen, et al., "Identification of HIV–Ivpr Product and Function," J. AIDS (1990) 3:11–18.

Colmenares, et al., "The ski Oncogene Induces Muscle Differentiation in Quail Embryo Cells," Cell(1989) 59:293–303.

Connor, et al., "Vpr is Required for Efficient Replication of Human Immunodeficiency Virus Type–1 in Mononuclear Phagocytes," Virology (1995) 206:935–944.

Dedera, et al., "Viral Protein R of Human Immunodeficiency Virus Types 1 and 2 is Dispensible for Replication and Cytopathogenecity in Lymphoid Cells," J. Virol. (1989) 63:3205–3208.

DiMarzo, et al., "Mutational Analysis of Cell Cycle Arrest, Nuclear Localization, and Virion Packaging of Human Immunodeficiency Virus Type I Vpr," J. Virol. (1995) 69:7909–7916.

Draper, et al., "CCR4 is a Glucose–Regulated Transcription Factor Whose Leucine–Rich Repeat Binds Several Proteins Important for Placing CCR4 in its Proper Promoter Context," Mol. Cell. Biol. 1994) 14:4522–4531.

Dubiel, et al., "Molecular cloning and expression of subunit 12:a non–MCP and non–ATPase subunit of the 26S protease," FEBS Lett. (1995) 363:97–100.

Fields, et al., "A Novel Genetic System to Detect Protein–Protein Interactions," Nature (1989) 340–245–246.

Fields, et al., "The Two–Hybrid System to Detect Protein–Protein Interactions," Methods: A Companion to Methods in Enzymology (1993) 5:116–124.

Fields, et al., The Two–Hybrid System: An Assay for Protein–Protein Interactions, Trends in Genetics, Aug 1994, 10(8)286–292.

Fisher, et al., "A molecular clone of HTLV–III with biological activity," Nature (1985) 316:262–265.

Flethcher, et al., "Nuclear import and cell cycle arrest functions of the HIV–1 Vpr protein are encoded by two separate genes in HIV–2/SIV–sm," EMBO J. (1996) 15:6155–6165.

Fuerst, et al., "Use of a Hybrid Vaccina Virus–T7 RNA Polymerase System for Expression of Target Genes," Mol. Cell. Biol. (1987) 7:2538–2544.

Gallo, et al., "Frequent Detection and Isolation of Cytopathic Retrovirus (HTLV–III) from Patients with AIDS and at Risk for AIDS," Science (1984) 224:500–503.

Garrett, et al., "Rev Activates Expression of the Human Immunodeficiency Virus Type 1 vif and vpr Gene Products," J. Virol.(1991) 65:1653–1657.

Gras–Masse, et al., "A Synthetic Protein Corresponding to the Entire VPR Gene Product from the Human Immunodeficiency Virus HIV–1 is Recognized by Antibodies form HIV–Infected Patients," Intl. J. Peptide Protein Res. (1990) 36:219–226.

Gridley, et al., "Molecular Analysis of the Move 34 Mutation: Transcript Disrupted by proviral Integration in Mice is Conserved in Drosophila," Development (1990) 109:235–242.

Gridley, et al., "The murine Mov–34 gene: Full length cDNA and genomic organization," Genomics (1991) 11:501–507.

Griffin, et al., "Activation of HIV gene expression during monocyte differentiation by induction of NF–kappaB," Nature (339) 70–73.

Frigerio, et al, "Cloning, sequencing and expression of the L5, L21, L27a, L28, S5, S9, S10 and S29 human ribosomal protein mRNAs," Biochim. Biophys. Acta (1995) 1262:64–68.

Harada, et al., "Tumor Promoter, TPA, Enhances Replication of HTLA–III/LAV," Virology (1986) 154:249–258.

Hattori, et al., "The human immunodeficiency virustype 2 genesis essential for production infection of human macrophages," Proc. Natl. Acad. Sci. USA (1990) 87:8080–8084.

He, et al., "Human Immunodeficiency Virus Type 1 Viral Protein R (Vpr) Arrests Cells in the G2 Phase of the Cell Cycle by Inhibiting p34–cdc2 Activity," J. Virol. (1995) 69(11):6705–6711.

Heinzinger, et al., "The Vpr protein of human immunodeficiency virus type 1 influences nuclear localization of viral nucleic acids in nondividing host cells," Proc. Natl. Acad. Sci. USA (1994) 91:7311–7315.

Hiti, et al., "Expression of the MyoD1 Muscle Determination Gene Defines Differentiation Capability but not Tumorigenicity of Human Rhabdomyosarcomas," Mol. Cell Biol. (1989) 9(11):4722–4730.

Ho, et al., "Site–Directed Mutagenesis by Overlap Extension Using the Polymerase chain Reaction," Gene (1989) 77:51–59.

Jowett, et al., "The Human Immunodeficiency Virus Type 1 vpr Gene Arrests Infected T Cells in the G2 + M Phase of the Cell Cycle," J. Virol. (1995) 69:6304–6313.

Kent, et al., Synthetic Peptides in Biology and Medicine (1985) Alioto, et al, eds., Elsevier Science Publishers, Amsterdam, p. 29–57.

Korber, et al., "Signature Pattern Analysis: A Method for Assessing Viral Sequence Relatedness," AIDS Res. Human Retrovirus (1992) 8(9):1549–1560.

Kozak, M., "Point Mutations Define a Sequence Flanking the AUG Initiator Codon that Modulates Translation by Eukaryotic Ribosomes" Cell (1986) 44:283–292.

Levy, et al., "Induction of Cell Differentiation by Human Immunodeficiency Virus 1 vpr," Cell (1993) 72:541–550.

Levy, et al, "Extracellular Vpr Protein Increases Cellular Permissiveness to Human Immunodeficiency Virus Replication and Reactivates Virus from Latency," J. Virol. (1995) 69(2): 1243–1252.

Levy, et al., "Isolation of Lymphocytopathic Retrovirus from San Francisco Patients with AIDS," Science (1984) 225:840–842.

Li, et al, "Human Immunodeficiency Virus Type 1 DNA Synthesis, Integration, and Efficient Viral Replication in Growth Arrested T Cells," J. Virol.(1993) 67:3969–3977.

Ling, et al., "Optimization of the Polymerase Chain Reaction with Regard to Fidelity: Modified T7, Taq, and Vent DNA Polymerases," PCR Methods and Applications (1991) 1:63–69.

Lu, et al., "Human Immunodeficiency Virus Type 1 Viral Protein R Localization in Infected Cells and Viruses," J. Virol. (1993) 67(11):6542–6550.

Macredie, et al., "A domain of human immunodeficiency virus type 1 Vpr containing repeated H(S/F)RIG amino acid motifs causes cell growth arrest and structural defects," Proc. Natl. Acad. Sci. USA (1995) 92:2770–2774.

Mahalingam, et al., "In vitro and In Vivo Tumor Growth Suppression," DNA Cell Biol. (1997) 16:137–143.

Mahalingham, et al., "Functional Analysis of HIV–1 Vpr: Identification of Determinants Essential for Subcellular Localization," Virology (1995) 212:331–339.

Mahalingam, et al., "Mutagenesis of the putative alpha–helical domain of the Vpr protein of human immunodeficiency virus type 1: Effect on stability and virion incorporation," Proc. Natl. Acad. Sci. USA (1990) 92:3794–3798.

Merrifield, R.B., "Solid Phase Peptide Synthesis. I. The Synthesis of a Tetrapeptide," J. Am. Chem. Soc. (1963) 15:2149–2154.

Morgenstern, et al., "Advanced mammallian gene transfer: high titre retroviral vectors with multiple drug selection markers and a complementary helper–free packaging cell line," Nuc. Acids Res. (1990) 18(12):3587–3596.

Murray, A.M.,"Creative blocks: cell–cycle checkpoints and feedback controls," Nature (1992) 359:599–604.

Myers, et al., "The Emergence of Simian/Human Immunodeficiency Viruses," AIDS Res. Human Retroviruses (1992) 8:373–386.

Norbury, et al., "Control of the higher eukaryote cell cycle by p34cdc2 homologues," Biochim. Biophys. Acta (1989) 989:85–95.

Neurath, et al, Eds., The Proteins, 1976, vol II, $3_{rd}$ Ed., Academic Press, NY.

Ogawa, et al., "Mutational Analysis of the Human Immunodeficiency Virus vpr Open Reading Frame," J. Virol. (1989) 63(9):4110–4114.

Meijer, et al., "Osjabl(Acc. #AF72849): A rice homolog of the human JAB1 transcriptional coactivator," Plant Physiol. (1998) 117:1526.

Pelicci, et al., "A family of Shc related proteins with conserved PTB, CH1 and SH2 regions," Oncogene (1996) 13:633–641.

Poirey, et al., "Sequencing analysis of a 36.8 kb fragment of yeast chromosome XV reveals 26 open reading frames including SEC63, CDC31, SUG2, GCD1, RBL2, PNT1, PAC1 and VPH1," Yeast (1997) 13:483–487.

Ratner, et al., "Complete Nucleotide Sequences of Functional Genes of the AIDS Virus," AIDS Res. Human Retrovirus ((1987) 3:57–69.

Ratner, et al., "Complete Nucleotide Sequences of Functional Genes of the AIDS Virus, HTLV–III," Nature (1985) 313(1):277–284.

Re, et al., "Human Immunodeficiency Virus Type 1 Vpr Arrests the Cell Cycle in G2 by Inhibiting the Activation of p34cdc2–Cyclin B," J. Virol. (1995) 69(11):6859–6864.

Refaeli, et al., "Recombinant HIV–1 Vpr Protein Induces Cellular Differentiation in Vitro," J. Cell Biochem. Supp 18B (1994) Keystone Symposia on Molecular & Cellular Biology 140:J262.

Refaeli, "The glucocorticoid receptor type II complex is a target of the HIV–1 cpr gene product," Proc. Natl. Acad. Sci USA (1995) 92:3621–3625.

Reiss, et al., "Antibody Response to Viral Proteins U (vpu) and R (vpr) in HIV–1 Infected Individuals," Acq. Immun. Defic. Synd. (1990) 3:115–122.

Rich, et al., "Increases Susceptibility of Differentiated Mononuclear Phagocytes to Productive Infection with Human Immunodeficiency Virus–1 (HIV–1)," Am. Soc. Clin. Invest., Inc. (1992) 89:176–183.

Rogel, et al., "The Human Immunodeficiency Virus Type 1 vpr Gene Prevents cell Proliferation During Chronic Infection," J. Virol. (1995) 69(2):882–888.

Rose, et al., "Frequent Identification of HIV–1 DNA in Bronchoalveolar Lavage cells Obtained from Individuals with the Acquired Immunodeficiency Syndrome," Am. Rev. Respir. Diseases (1991) 143:850–854.

Roulston, et al., "Induction of Monocytic Differention and NF–kappaB–like Activities by Human Immunodeficiency Virus 1 Infection of Myleomonoblastic Cells," J. Exp. Med.(1992) 175:751–763.

Salahuddin, et al., "Human T Lymphotrophic Virus Type III Infection of Human Alveolar Macrophages," Blood (1986) 68:281–284.

Sambrook, et al., Molecular Cloning: A Laboratory Manual, Cold Spring Harbor Laboratory, 1989, vol. 2, pp 10–59.

Sato, et al., "Identification and Localization of vpr Gene Product of Human Immunodeficiency Virus Type 1," Virus Genes (1990) 4(4):303–312.

Schuitemaker, et al., "Biological Phenotype of Human Immunodeficiency Virus Type 1 Clones at Different Stages of Infection: Progression of Disease is Associated with a Shift from Monocytotropic to T–Cell–Tropic Virus Populations," J. Virol. (1992) 66(3):1354–1360.

Shibata, et al., "Mutational Analysis of Simian Immunodeficiency Virus from African Green Monkeys and Human Immunodefiency Virus Type 2," J. Med. Primatol. (1990)19:217–225.

Shibata, et al., "Mutational Analysis of the Human Immunodeficiency Virus Type 2 (HIV–2) Genome in Relation to HIV–1 and Simian Immunodeficiency Virus SIV–AGM," J. Virol. (1990) 64(2):742–747.

Siegel, et al., "Morphological and biochemical differentiation of the human medulloblastoma cell line TE671," Devel. Brain Res. (1988) 44:269–280.

Starcich, et al., "Characterization of Long Terminal Repeat Sequence of HTLV–III," Science (1985) 227:538–540.

Stratton, et al., "Characterization of the Human Cell Line TE671," Carcinogenesis (1989) 10:899–905.

Tsurumi, et al., "cDNA cloning of p40, a regulatory subunit of the human 26S proteasome, and a homolog of the Mov–34 gene product," Biochem. Biophys. Res. Comm. (1995) 210:600–608.

Valentin et al., "In Vitro Maturation of Mononuclear Phagocytes and Susceptibility of HIV–1 Infection," J. Acquired-Immun. Def. Synd. (1991) 4:751–759.

Voller, et al., eds., "Immunoassays for the 80's", University Park, 1981.

Weiner et al., "Linkage of tyrosine kinase activity with transforming ability of the p185neu oncoprotein," Oncogene (1989) 4:1175–1183.

Westerveldt, et al., "Dual Regulation of Silent and Productive Infection in Monocytes by Distinct Human Immunodeficiency Virus Type 1 Determinants," J. Virol. (1992) 66(6):3925–3931.

Wide, L., "Solid phase antigen–antibody systems", in "Radioimmunology Methods", (1970) Churchill Livinstone, Edinburgh and London, pp. 405–412.

Wong–Staal et al., "Human Immunodeficiency Virus: The Eighth Gene," AIDS Res. Human Retrovirus (1987) 3(1):33–39.

Work, et al., "Laboratory Techniques and Biochemistry in Molecular Biology", North Holland Pub. Co., NY, 1978.

Yu et al., "Open Reading Frame vpr of Simian Immunodeficiency Virus Encodes a Virion–Associated Protein," J. Virol. (1990) 64(11)5688–5693.

Yuan et al., "Human Immunodeficiency Virus vpr Gene Encodes a Virion–Associated Protein," AIDS Res. Human Retrovirus (1990) 6(11):1265–1271.

Zack et al., "HIV–1 Production from Infected Peripheral Blood T Cells after HTLV–I Induced Mitogenic Stimulation," Science (1988) 240:1026–1029.

* cited by examiner

Figure 1A

| | | |
|---|---|---|
| 1 | M H A R A A A S V M D I C R I R L D H A V S M S T | 25 |
| 26 | F F F F L S S G M E V D A A V V P S V M A C G V T | 50 |
| 51 | G S V S V A L H P L V I L N I S D H W I R M R S H | 75 |
| 76 | Q G R P V Q V I G A L I G K Q E G R N I E V M N S | 100 |
| 101 | F E L L S H T V E E K I I D K E Y Y Y T K E E Q | 125 |
| 126 | F K Q V F K E L E F L G W Y T T G G P P D P S D I | 150 |
| 151 | H V H K Q C C E I I E S P L F L K L N P M T K H T | 175 |
| 176 | D L P V S V F E S V I D I I N G E A T M L F A E L | 200 |
| 201 | T Y T L A T E E A E R I G V D H V A R M T A T G S | 225 |
| 226 | G E N S T V A E H L I A Q H S A I K M L H S R V K | 250 |
| 251 | L I L E Y V K A S E A G E V P F N H E I L R E A Y | 275 |
| 276 | A L C H C L P V L S T D K F K T D F Y D Q C N D V | 300 |
| 301 | G L M A Y L G T I T K T C N T M N Q F V N K F N V | 325 |
| 326 | L Y D R Q G I G R R M R G L F F * | 341 |

Figure 4A

| | | Subcellular colocalization by immunofluorescence | | Cell cycle arrest at G2/M |
|---|---|---|---|---|
| 19 | 78 | Vpr | hVIP | |
| TLELLEELKNEAVRHFPRIWLHSLGQHIYETYGDIWTGVEALIRILQQLLFIHFRIGCRH | | NM | NM | + |
| ----------L------------------------------------------------ | | N | N | – |
| -A-AA--A---------------------------------------------------- | | C | C | + |
| ---------------------------P-------------------------------- | | N/C | N | – |
| --------------------------------S--------------------------- | | C | N | – |
| -----------------------------------------C------------------ | | N/C | N | – |
| -------------------------------------------------A---------- | | N | N | – |
| ------------------------------------------------------S----- | | N/C | N | – |

CELLULAR RECEPTOR FOR HIV-1 VPR ESSENTIAL FOR G2/M PHASE TRANSITION OF THE CELL CYCLE

CROSS-REFERENCE TO RELATED APPLICATIONS

The present application is a continuation of U.S. Ser. No. 09/529,245 filed Oct. 17, 2000, now U.S. Pat. No. 6,448,078, which is the U.S. national phase of international Application No. PCT/US98/21432 filed Oct. 9, 1998, which is a continuation of U.S. Ser. No. 08/949,202 filed on Oct. 10, 1997, now U.S. Pat. No. 6,060,587, each of which is incorporated herein by reference in its entirety.

FIELD OF THE INVENTION

The invention relates to the identification and cloning of human Vpr Interacting Protein (hVIP), to methods of making and using the same, and to compositions and methods of inhibiting their activity in the cell cycle.

BACKGROUND OF THE INVENTION

Relatively little regarding the function of the viral protein R (Vpr) has been reported since the demonstration that the small open reading frame within HIV-1 designated R encodes a 15 kd protein. Wong-Staal, et al., *AIDS Res. Hum. Retroviruses*, 1987, 3, 33–39. The vpr open reading frame is conserved within all genomes of HIV-1 and HIV-2 and within most, if not all, simian immunodeficiency virus (SIV) genomes. Vpr is immunogenic in vivo and most if not all HIV$^+$ individuals makes antibodies that can react with eukaryotically produced Vpr protein.

The progression from HIV infection to AIDS is in large part determined by the effects of HIV on the cells that it infects, including CD4$^-$ T lymphocytes and macrophages. On the other hand, cell activation, differentiation and proliferation are in turn thought to regulate HIV infection and replication in T cells and macrophages. Gallo, et al., *Science*, 1984, 224, 500; Levy, et al., *Science*, 1984, 225, 840; Zack, et al., *Science*, 1988, 240, 1026; Griffin, et al., *Nature*, 1988, 339, 70; Valentin, et al., *J. AIDS*, 1991, 4, 751; Rich, et al., *J. Clin. Invest.*, 1992, 89, 176; and Schuitemaker, et al., *J. Virol.*, 1992, 66, 1354. Cell division per se may not be required since HIV and other lentiviruses can replicate in nonproliferating, terminally differentiated macrophages and growth-arrested T lymphocytes. Rose, et al., *Am. Rev. Respir. Dis.*, 1986, 143, 850; Salahuddin, et al., *Blood*, 1986, 68, 281; and Li, et al., *J. Virol.*, 1993, 67, 3969. The ability of lentiviruses, including HIV, to replicate in nonproliferating cells, particularly in macrophages, is believed to be unique among retroviruses and it may be significant that several lentiviruses contain a vpr-like gene. Myers, et al. *AIDS Res. Hum. Retrovir.*, 1992, 8, 373. HIV infection of myeloid cell lines can result in a more differentiated phenotype and increase the expression of factors such as NF-KB which are necessary for HIV replication. Roulston, et al., *J. Exp. Med.* 1992, 175, 751; and Chantal Petit, et al., *J. Clin. Invest.*, 1987, 79, 1883.

The most evidence for the function of the Vpr protein comes from several studies reporting the activities of HIV strains that have mutations in the vpr gene. It has been reported that mutations in the vpr gene results in a decrease in the replication and cytopathogenicity of HIV-1, HIV-2, and SIV in primary CD4$^-$T lymphocytes and transformed T cell lines (Ogawa, et al., *J. Virol.*, 1989, 63, 4110–4114; Shibata, et al. *J. Med. Primatol.*, 1990a, 19, 217–225; Shibata, et al., *J. Virol.*, 1990b, 64, 742–747 and Westervelt, et al., *J. Virol.*, 1992, 66, 3925), although others have reported mutated vpr gene had no effect on replication (Dedera, et al., *Virol.*, 1989, 63, 3205–3208). Interestingly HIV-2 mutated for vpr has been reported unable to infect primary monocyte/macrophages. Hattori, et al., *Proc. Natl. Acad. Sci. USA*, 1990, 87, 8080–8084. Transactivation of the HIV long terminal repeat and heterologous promoters by HIV is increased about 3-fold in wild-type versus vpr-negative HIV-1, though the mechanism through which Vpr may transactivate transcription is unknown and may be indirect. Cohen, et al., *J. Acquir. Immune Defic. Syndr.*, 1990b, 3, 11–18. The relationship between the effects of Vpr on promoter activity and viral infectivity is not clear. Vpr protein is incorporated into the viral particle, and this finding has led to the proposition that Vpr functions early in infection, following virus penetration and uncoating, and that Vpr may interact with cellular regulatory mechanisms important in the establishment of infection. Cohen, et al., *J. Virol.*, 1990a, 64, 3097–3099; Yu, et al., *J. Virol.*, 1990, 64, 5688–5693; and, Yuan, et al., *AIDS Res. Hum. Retroviruses*, 1990, 6, 1265–1271.

The vpr gene of HIV-1 has been shown to induce cellular growth inhibition and differentiation in tumor lines of intermediate differentiation in vitro Levy, et al., *Cell*, 1993, 72, 541. Since Vpr protein originates within viral particles. Vpr may play a role in establishing productive infection. In addition, several important possibly interrelated functions have been identified for HIV-1 Vpr. These include import of reverse transcription complex into the nucleus of non-dividing cells, cellular differentiation, cell cycle arrest at the G2/M phase, and enhancement of HIV-1 replication.

HIV-1 Vpr is required to import the viral preintegration complex into the nucleus of non-dividing cells (Heinzinger, et al., *Proc. Natl. Acad. Sci. USA*, 1994, 91, 7311–7315; and Fletcher, et al., *EMBO.*, 1996, 15, 6155–6165) and it enhances viral replication in monocyte cell lines (Balotta, et al., *J. Virol.*, 1993, 67, 4409–4414; Balliet, et al., *Virology*, 1994, 200, 623–631; and Connor, et al., *Virology*, 1995, 206, 935–944). Vpr localizes to the nucleus and induces cellular differentiation subsequently arresting cells at the G2/M phase of the cell cycle. Lu, et al., *J. Virol.*, 1993, 67, 6542–6550; Mahalingam, et al., *Virology*, 1995, 212, 331–339; DiMarzio, et. al., *J. Virol.*, 1995, 69, 7909–7916; Levy, et al., *Cell*, 1993, 72, 541–550; Rogel, et al., *J. Virol.*, 1995, 69, 882–888; Jowett, et al., *J. Virol.*, 1995, 69, 6304–6313; Mahalingam, et al., DNA *Cell Biol.*, 1997, 16, 137–153. Mutational analysis suggests that the functions of this 96 amino acid Vpr protein are mediated through interactions with appropriate cellular cofactor(s). Zhao, et al., *J. Biol. Chem.*, 199, 269, 15577–15582; Refaeli, et al., *Proc. Natl. Acad. Sci. USA*, 1995, 92, 3621–3625; He, et al., *J. Virol.*, 1995, 69, 6705–6711; Re, et al., *J. Virol.*, 1995, 69, 6859–6864.

There is a need to identify novel compounds which inhibit HIV replication. Specifically, safe and effective compounds are sought which reduce replication by interfering with particular molecular signals mediated by Vpr. Likewise, safe and effective compounds are sought which interfere with the cofactor with which Vpr interacts, which is an essential component of the cell cycle cascade. Moreover, there is a need to identify the co-factor and target it in methods of modulating the cell cycle. There is a need for compounds and methods for inhibiting the progression of the cell cycle from G2 to M phase in cells whose proliferation is undesirable such as hyperproliferating cells.

SUMMARY OF THE INVENTION

In the present invention, a yeast two-hybrid assay was utilized in an effort to identify specific cellular cofactors which interact with Vpr. Three clones that fulfilled criteria essential for a Vpr ligand, containing overlapping complementary DNA derived from the same gene, were isolated. The protein encoded by this cDNA was designated hVIP. Various Vpr mutants were tested for the ability to arrest the cell cycle and colocalize with hVIP in different human cell lines. A direct correlation was found between the inhibition of cellular proliferation and the colocalization of Vpr mutants with hVIP. Suppression of hVIP expression in cycling cells arrest cells in G2/M phase. hVIP was found to be necessary for the transition from G2 to M phase and therefore is an essential component of the cell cycle cascade.

The present invention relates to substantially pure hVIP, and fragments thereof.

The present invention relates to isolated nucleic acid molecules that encode hVIP, or a fragment thereof.

The present invention relates to nucleic acid probes and primers directed to nucleic acid molecules that encode hVIP, or a fragment thereof.

The present invention relates to oligonucleotide molecules that consist of a nucleotide sequence complementary to a portion of the nucleotide sequence that encodes hVIP.

The present invention relates to vectors comprising nucleic acid molecules encoding hVIP.

The present invention relates to recombinant expression vectors that comprise nucleic acid sequences that encode hVIP, The present invention relates to host cells that comprise recombinant expression vectors which include nucleic acid sequences that encode hVIP.

The present invention relates to genetic therapy vectors comprising nucleic acid molecules encoding hVIP.

The present invention relates to isolated antibody which binds to an epitope on hVIP.

The present invention relates to pharmaceutical compositions comprising a pharmaceutically acceptable carrier and nucleic acid molecules complementary to a portion of hVIP.

The present invention is related to methods of making hVIP.

The present invention is related to methods of inhibiting expression of human Vpr Interacting Protein with oligonucleotides complementary to a portion of the nucleotide sequence that encodes hVIP.

The present invention relates to fragments of Vpr which interact with hVIP to prevent or inhibit G2/M transition by cells.

The present invention relates to pharmaceutical compositions which comprise fragments of Vpr which interact with hVIP to prevent or inhibit G2/M transition by cells.

The present invention relates to isolated nucleic acid molecules that encode fragments of Vpr which interact with hVIP to prevent or inhibit G2/M transition by cells.

The present invention relates to vectors comprising nucleic acid molecules encoding fragments of Vpr which interact with hVIP to prevent or inhibit G2/M transition by cells.

The present invention relates to recombinant expression vectors that comprise nucleic acid sequences that encode fragments of Vpr which interact with hVIP to prevent or inhibit G2/M transition by cells.

The present invention relates to host cells that comprise recombinant expression vectors which include nucleic acid sequences that encode fragments of Vpr which interact with hVIP to prevent or inhibit G2/M transition by cells.

The present invention relates to genetic therapy vectors comprising nucleic acid molecules encoding fragments of Vpr which interact with hVIP to prevent or inhibit G2/M transition by cells.

The present invention is related to methods of making fragments of Vpr which interact with hVIP to prevent or inhibit G2/M transition by cells.

The present invention is related to methods of inhibiting cells from transitioning from M to G2 comprising contacting cells with a fragments of Vpr which interact with hVIP to prevent or inhibit G2/M transition by cells or a nucleotide sequence that encodes fragments of Vpr which interact with hVIP to prevent or inhibit G2/M transition by cells which is expressed by the cells.

The present invention relates to methods of identifying anti-HIV compounds that comprise the steps of contacting hVIP or a fragment of HIV known to interact with Vpr with Vpr or a fragment of Vpr which interacts with hVIP to prevent or inhibit G2/M transition by cells in the presence of a test compound and comparing the affinity of hVIP or fragment thereof with Vpr or fragment thereof to the affinity of hVIP or fragment thereof with Vpr or fragment thereof in the absence of a test compound.

BRIEF DESCRIPTION OF THE FIGURES

FIGS. 4A and 4V show colocalization and interaction of hVIP with HIV-1 Vpr mutants. FIG. 4A shows mutant Vpr molecules were generated by overlap PCR as described previously (Mahalingam, et al., *Virology*, 1995, 212, 331–339; and Ho, et al., *Gene*, 1989, 77, 51–59).

FIG. 5A shows human embryonal rhabdomyosarcoma (RD) cells which were transfected with Vpr, HVIP sense, and antisense expression vectors and the cells were maintained in DMEM media containing 2 μg/ml puromycin. The cells were photographed five to seven days later using a Nikon phase contrast microscope. Panel a shows control vector pBabepuro; panel b shows Vpr; panel c shows hVIP sense; and panel d shows hVIP antisense. FIG. 5B shows the transfected RD cells were stained with propidium iodide and used for flow cytometric analysis as described previously (Mahalingam, et al., DNA *Cell Biol.*, 1997, 16, 137–153). RD cells expressing Vpr and HVIP antisense arrest at G2/M phase of the cell cycle with 4 n DNA content.

DETAILED DESCRIPTION OF THE INVENTION

Figure 1B:
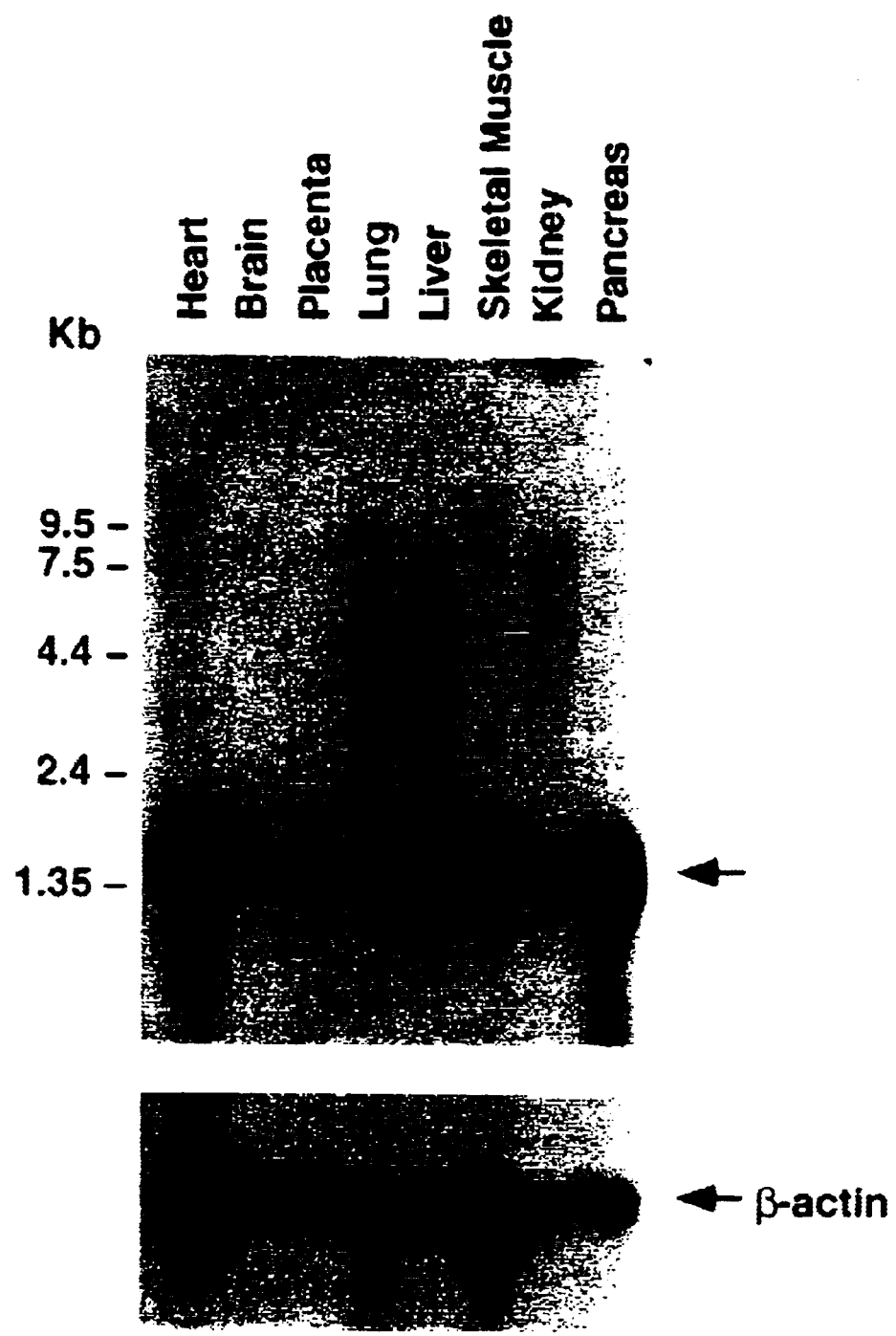
FIG. 1B shows a Northern blot of Poly (A)$^+$ RNA from a variety of human organs and the RNA from CEM, RD and PBMCs were probed with a $^{32}$P-labeled hVIP fragment.

A new human Vpr-associated protein, human Vpr Interacting Protein (hVIP), has been discovered. This protein localizes to the nucleus and functions as an essential component of the cell cycle cascade. An association between the induction of cell cycle arrest at G2/M phase by Vpr and a change in the subcellular localization of hVIP from a nuclear to a perinuclear pattern is demonstrated. Accordingly, it appears that hVIP is a cellular cofactor of Vpr and their specific interaction is essential for the cell cycle arrest activity of Vpr. Thus, inhibition of hVIP will inhibit cell division.

A number of diseases are characterized by a loss of control of the cell cycle and a resultant uncontrolled cell division. Uncontrolled cell proliferation is a primary characteristic of all forms of cancer as well as psoriasis, hyperplasia and other diseases and disorders characterized by cell proliferation. The ability to block cell division by inhibiting the activity of hVIP thereby provides a means to treat individuals suffering from diseases and disorders characterized by uncontrolled cell proliferation and HIV. The discovery of hVIP, and that it plays a role in the cell cycle, provides drug targets against which inhibitors can be identified and/or designed. Such inhibitors are useful to block cell division, which is a particular strategy for anti-cancer or anti-HIV drugs.

hVIP has been purified; complexes which include the protein have been isolated; hybridomas which produce antibodies that bind to the proteins can be generated; cDNAs that encode this protein have been isolated, sequenced, incorporated into vectors including expression vector which were introduced into host cells that then express the proteins recombinantly. Antisense oligonucleotide molecules against hVIP have been generated.

The discovery of hVIP provides the means to design and discover specific inhibitors. According to the present invention, hVIP may be used to screen compounds for specific inhibitors. Inhibitors are useful as anti-cancer and anti-HIV agents. Purified hVIP, and complexes which include hVIP, may be used in drug screens to determine whether or not these proteins and complexes are active in the presence of test compounds. Test compounds may be screened to identify compounds which dissociate the complexes and inhibit the formation of complexes.

Isolated cDNA that encodes hVIP is useful as a starting material in the recombinant production of hVIP. The cDNA is incorporated into vectors including expression vectors which are introduced into host cells that then express the proteins recombinantly. Nucleic acid molecules and fragments thereof, particularly genomic sequences may be used as probes to detect genetic rearrangements. Probes are useful, for example, in restriction fragment length polymorphism assays and fluorescence in situ hybridization assays. Nucleic acid molecules which comprise a nucleotide sequence which are complementary to fragments of the cDNA that encode hVIP may be used as antisense molecules and primers to inhibit translation of mRNA and amplify genetic sequences, respectively.

hVIP is encoded by cDNA shown in SEQ ID NO:1 and has an amino acid sequence shown in SEQ ID NO:2. hVIP can be isolated from natural sources, produced by recombinant DNA methods or synthesized by standard protein synthesis techniques. Fragments of the full length hVIP are described in parent application Ser. No. 08/593,695 filed Jan. 29, 1996, which is incorporated herein by reference.

Using standard techniques and readily available starting materials, a nucleic acid molecule that encodes hVIP may be isolated from a cDNA library, using probes and primers which are designed using the nucleotide sequence information disclosed in SEQ ID NO:1. The present invention relates to an isolated nucleic acid molecule that comprises a nucleotide sequence that encodes hVIP. The present invention relates to an isolated nucleic acid molecule that comprises a nucleotide sequence that encodes the amino acid sequence of SEQ ID NO:2, or a fragment thereof In some embodiments, the nucleic acid molecules consist of a nucleotide sequence that encodes hVIP. In some embodiments, the nucleic acid molecules comprise the nucleotide sequence that consists of the coding sequence in SEQ ID NO:1. In some embodiments, the nucleic acid molecules consist of the nucleotide sequence set forth in SEQ ID NO:1. The isolated nucleic acid molecules of the invention are useful to prepare constructs and recombinant expression systems for preparing proteins of the invention.

A cDNA library may be generated by well known techniques. A cDNA clone which contains one of the nucleotide sequences described herein may be identified using probes or primers that comprise at least a portion of the nucleotide sequence disclosed in SEQ ID NO:1. The probes or primers have at least 16 nucleotides, preferably at least 24 nucleotides. The probes or primers are used to screen the cDNA library using standard hybridization techniques. Alternatively, genomic clones may be isolated using genomic DNA from any human cell as a starting material.

The present invention relates to isolated nucleic acid molecules that comprise a nucleotide sequence identical or complementary to a fragment of SEQ ID NO:1 which is at least 10 nucleotides. In some embodiments, the isolated nucleic acid molecules consist of a nucleotide sequence identical or complementary to a fragment of SEQ ID NO:1 which is at least 10 nucleotides. In some embodiments, the isolated nucleic acid molecules comprise or consist of a nucleotide sequence identical or complementary to a fragment of SEQ ID NO:1 which is 15–150 nucleotides. In some embodiments, the isolated nucleic acid molecules comprise or consist of a nucleotide sequence identical or complementary to a fragment of SEQ ID NO:1 or which is 15–30 nucleotides. Isolated nucleic acid molecules that comprise or consist of a nucleotide sequence identical or complementary to a fragment of SEQ ID NO:1 which is at least 10 nucleotides are useful as probes for identifying genes and cDNA sequence having SEQ ID NO:1. PCR primers for amplifying genes and cDNA having SEQ ID NO:1, and antisense molecules for inhibiting transcription and translation of genes and cDNA, respectively, which encode hVIP having the amino acid sequence of SEQ ID NO:2.

The cDNA that encodes hVIP may be used as a molecular marker in electrophoresis assays in which cDNA from a sample is separated on an electrophoresis gel and hVIP probes are used to identify bands which hybridize to such probes. Specifically, SEQ ID NO:1, or portions thereof, may be used as a molecular marker in electrophoresis assays in which cDNA from a sample is separated on an electrophoresis gel and hVIP specific probes are used to identify bands which hybridize to them, indicating that the band has a nucleotide sequence complementary to the sequence of the probes. The isolated nucleic acid molecule provided as a size marker will show up as a positive band which is known to hybridize to the probes and thus can be used as a reference point to the size of cDNA that encodes hVIP. Electrophoresis gels useful in such an assay include standard polyacrylamide gels as described in Sambrook et al., *Molecular Cloning a Laboratory Manual,* Second Ed. Cold Spring Harbor Press (1989) which is incorporated herein by reference.

The nucleotide sequences in SEQ ID NO:1 may be used to design probes, primers and complementary molecules which specifically hybridize to the unique nucleotide sequences of hVIP. Probes, primers and complementary molecules which specifically hybridize to nucleotide sequence that encodes hVIP may be designed routinely by those having ordinary skill in the art.

The present invention also includes labeled oligonucleotides which are useful as probes for performing oligonucleotide hybridization methods to identify hVIP. Accordingly, the present invention includes probes that can be labeled and hybridized to unique nucleotide sequences of hVIP. The labeled probes of the present invention are labeled with radiolabelled nucleotides or arc otherwise detectable by readily available nonradioactive detection systems. In some preferred embodiments, probes comprise oligonucleotides consisting of between 10 and 100 nucleotides. In some preferred, probes comprise oligonucleotides consisting of between 10 and 50 nucleotides. In some preferred, probes comprise oligonucleotides consisting of between 12 and 20 nucleotides. The probes preferably contain nucleotide sequence completely identical or complementary to a fragment of a unique nucleotide sequences of hVIP. In some embodiments, labeled probes are used to determine on which chromosome the hVIP gene is present. Such labeled probes comprise some or all of SEQ ID NO:1.

The cDNA that encodes hVIP may be used to design PCR primers for amplifying nucleic acid sequences. PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990) which is incorporated herein by reference. Applications of PCR technology are disclosed in "Polymerase Chain Reaction" Erlich, H. A., et al., Eds. Cold Spring Harbor Press, Cold Spring Harbor, N.Y. (1989) which is incorporated herein by reference. Some simple rules aid in the design of efficient primers. Typical primers are 18–28 nucleotides in length having 50% to 60% g+c composition. The entire primer is preferably complementary to the sequence it must hybridize to. Preferably, primers generate PCR products 100 base pairs to 2000 base pairs. However, it is possible to generate products of 50 base pairs to up to 10 kb and more.

PCR technology allows for the rapid generation of multiple copies of nucleotide sequences by providing 5' and 3' primers that hybridize to sequences present in a nucleic acid molecule, and further providing free nucleotides and an enzyme which fills in the complementary bases to the nucleotide sequence between the primers with the free nucleotides to produce a complementary strand of DNA. The enzyme will fill in the complementary sequences adjacent to the primers. If both the 5' primer and 3' primer hybridize to nucleotide sequences on the complementary strands of the same fragment of nucleic acid, exponential amplification of a specific double-stranded product results. If only a single primer hybridizes to the nucleic acid molecule, linear amplification produces single-stranded products of variable length.

The present invention relates to a vector or a recombinant expression vector that comprises a nucleotide sequence that encodes hVIP that comprises the amino acid sequence of SEQ ID NO:2. As used herein, the term "recombinant expression vector" is meant to refer to a plasmid, phage, viral particle or other vector which, when introduced into an appropriate host, contains the necessary genetic elements to direct expression of the coding sequence that encodes hVIP.

One having ordinary skill in the art can isolate the nucleic acid molecule that encodes hVIP and insert it into an expression vector using standard techniques and readily available starting materials. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences. In some embodiments, the recombinant expression vector comprises the nucleotide sequence set forth in SEQ ID NO:1. The recombinant expression vectors of the invention are useful for transforming hosts which express hVIP.

The present invention relates to a host cell that comprises the recombinant expression vector that includes a nucleotide sequence that encodes hVIP that comprises SEQ ID NO:1. In some embodiments, the host cell comprises a recombinant expression vector that comprises SEQ ID NO:1. Host cells for use in well known recombinant expression systems for production of proteins are well known and readily available. Examples of host cells include bacteria cells such as *E. coli,* yeast cells such as *S. cerevisiae,* insect cells such as *S. frugiperda,* non-human mammalian tissue culture cells chinese hamster ovary (CHO) cells and human tissue culture cells such as HeLa cells.

In some embodiments, for example, one having ordinary skill in the art can, using well known techniques, insert DNA molecules into a commercially available expression vector for use in well known expression systems. For example, the commercially available plasmid pSE420 (Invitrogen, San Diego, Calif.) may be used for production of hVIP in *E. coli.* The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA I or pcDNA3 (Invitrogen, San Diego, Calif.) may, for example, be used for production in mammalian cells such as Chinese Hamster Ovary cells. One having ordinary skill in the art can use these commercial expression vectors and systems or others to produce hVIP routine techniques and readily available starting materials. (See e.g., Sambrook et al., *Molecular Cloning a Laboratory Manual,* Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al. *Molecular Cloning a Laboratory Manual*, Second Ed. Cold Spring Harbor Press (1989).

The expression vector including the DNA that encodes hVIP is used to transform the compatible host which is then cultured and maintained under conditions wherein expression of the foreign DNA takes place. The protein of the present invention thus produced is recovered from the culture, either by lysing the cells or from the culture medium as appropriate and known to those in the art. One having ordinary skill in the art can, using well known techniques, isolate hVIP that is produced using such expression systems. The methods of purifying hVIP from natural sources using antibodies which specifically bind to hVIP as described above, may be equally applied to purifying hVIP produced by recombinant DNA methodology.

Examples of genetic constructs include the hVIP coding sequence operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes hVIP from readily available starting materials. Such gene constructs are useful for the production of hVIP.

In addition to producing hVIP by recombinant techniques, automated peptide synthesizers may also be employed to produce hVIP. Such techniques are well known to those having ordinary skill in the art and are useful if derivatives which have substitutions not provided for in DNA-encoded protein production.

Nucleic acid molecules that encode hVIP may be delivered using any one of a variety of delivery components, such as recombinant viral expression vectors or other suitable delivery means, so as to affect their introduction and expression in compatible host cells. In general, viral vectors may be DNA viruses such as recombinant adenoviruses and recombinant vaccinia viruses or RNA viruses such as recombinant retroviruses. Other recombinant vectors include recombinant prokaryotes which can infect cells and express recombinant genes. In addition to recombinant vectors, other delivery components are also contemplated such as encapsulation in liposomes, transferrin-mediated transfection and other receptor-mediated means. The invention is intended to include such other forms of expression vectors and other suitable delivery means which serve equivalent functions and which become known in the art subsequently hereto.

In a preferred embodiment of the present invention, DNA is delivered to competent host cells by means of an adenovirus. One skilled in the art would readily understand this technique of delivering DNA to a host cell by such means. Although the invention preferably includes adenovirus, the invention is intended to include any virus which serves equivalent functions.

In another preferred embodiment of the present invention, RNA is delivered to competent host cells by means of a retrovirus. One skilled in the art would readily understand this technique of delivering RNA to a host cell by such means. Any retrovirus which serves to express the protein encoded by the RNA is intended to be included in the present invention.

In another preferred embodiment of the present invention, nucleic acid is delivered through folate receptor means. The nucleic acid sequence to be delivered to a host cell is linked to polylysine and the complex is delivered to the tumor cell by means of the folate receptor. U.S. Pat. No. 5,108,921 issued Apr. 28, 1992 to Low et al., which is incorporated herein by reference, describes such delivery components.

The present invention also relates to a transgenic non-human mammal that comprises the recombinant expression vector that comprises a nucleic acid sequence that encodes hVIP that comprises the amino acid sequence of SEQ ID NO:2. Transgenic non-human mammals useful to produce recombinant proteins are well known as are the expression vectors necessary and the techniques for generating transgenic animals. Generally, the transgenic animal comprises a recombinant expression vector in which the nucleotide sequence that encodes hVIP is operably linked to a mammary cell specific promoter whereby the coding sequence is only expressed in mammary cells and the recombinant protein so expressed is recovered from the animal's milk. In some embodiments, the coding sequence that encodes hVIP is SEQ ID NO:1.

In some embodiments of the invention, transgenic non-human animals are generated. The transgenic animals according to the invention contain SEQ ID NO:1 under the regulatory control of a mammary specific promoter. One having ordinary skill in the art using standard techniques, such as those taught in U.S. Pat. No. 4,873,191 issued Oct. 10, 1989 to Wagner and U.S. Pat. No. 4,736,866 issued Apr. 12, 1988 to Leder, both of which are incorporated herein by reference, can produce transgenic animals which produce hVIP. Preferred animals are rodents, particularly goats, rats and mice.

The present invention is also directed to methods of inhibiting the expression of hVIP with oligonucleotides complementary to hVIP nucleic acid molecules. Oligonucleotides may comprise nucleotide sequences sufficient in identity and number to effect specific hybridization with a particular nucleic acid molecule. Such oligonucleotides are commonly described as "complementary to MRNA." Oligonucleotides may also be directed to nucleotide sequences within the genome. Oligonucleotides are commonly used as research reagents and diagnostics. Oligonucleotides have been employed as therapeutic moieties in the treatment of disease states in animals and man.

According to the present invention, preferred intragenic site for antisense oligonucleotides is the region encompassing the translation initiation or termination codon of the open reading frame (ORF) of the gene. Other target regions include the 5' untranslated region (5'UTR) and the 3' untranslated region (3'UTR). mRNA splice sites may also be preferred target regions. Once the target site has been identified, oligonucleotides are chosen which are sufficiently complementary to the target, i.e., hybridize sufficiently well and with sufficient specificity, to give the desired effect.

According to the present invention, "oligonucleotide" refers to oligomer(s) or polymer(s) of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Modified or substituted oligonucleotides are often preferred because of desirable properties such as, for example, enhanced cellular uptake, enhanced affinity for nucleic acid target and increased stability In the presence of nucleases.

Preferred oligonucleotides include, for example, phosphorothioates, phosphotriesters, and methyl phosphonates. Oligonucleotides may also contain one or more substituted sugar moieties including, but not limited to, 2'-OH, halogen, and alkyl. Oligonucleotides of the invention may also include nucleobase modifications or substitutions. As used herein, "unmodified" or "natural" nucleobases include adenine (A), guanine (G), thymine (T), cytosine (C) and uracil (U). Modified nucleobases include, for example, hypoxanthine, 6-methyladenine, 5-me pyrimidines, 2-aminoadenine, and the like.

The oligonucleotides in accordance with this invention may comprise from about 8 to about 150 nucleotides. More preferably, the oligonucleotides preferably comprise from about 8 to about 100 nucleotides. More preferably, the oligonucleotides preferably comprise from about 8 to about 50 nucleotides. More preferably, the oligonucleotides preferably comprise from about 8 to about 30 nucleotides. It is more preferred that such oligonucleotides comprise from about 12 to 25 nucleotides.

The oligonucleotides of the present invention can be utilized as diagnostics, therapeutics and as research reagents and kits. For therapeutics, an animal, preferably a human, suspected of having a disease or disorder which can be treated by modulating the expression of hVIP is treated by administering oligonucleotides in accordance with this invention. The oligonucleotides of the invention can be utilized in pharmaceutical compositions by adding an effective amount of an oligonucleotide to a suitable pharmaceutically acceptable diluent or carrier. Use of the oligonucleotides and methods of the invention may also be useful prophylactically.

The oligonucleotides of the present invention can be used as diagnostics for the presence of hVIP-specific nucleic acids in a cell or tissue sample. For example, radiolabeled oligonucleotides can be prepared by $^{32}$P labeling at the 5' end with polynucleotide kinase. Sambrook et al., *Molecular Cloning: A Laboratory Manual*, Cold Spring Harbor Laboratory, 1989, Volume 2, pg. 10.59. Radiolabeled oligonucleotides are then contacted with cell or tissue samples suspected of containing hVIP mRNA, and the samples are washed to remove unbound oligonucleotide. Radioactivity remaining in the sample indicates the presence of bound oligonucleotide, which in turn indicates the presence of nucleic acids complementary to the oligonucleotide, and can be quantitated using a scintillation counter or other routine means. Expression of nucleic acids encoding these proteins is thus detected.

Radiolabeled oligonucleotides of the present invention can also be used to perform autoradiography of tissues to determine the localization, distribution and quantitation of hVIP for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing an hVIP gene. Quantitation of the silver grains permits detection of the expression of mRNA molecules encoding hVIP proteins and permits targeting of oligonucleotides to these areas.

Oligonucleotides, or vectors producing the same, can be formulated into pharmaceutical compositions. Pharmaceutical compositions according to the invention include delivery components in combination with nucleic acid molecules which further comprise a pharmaceutically acceptable carriers or vehicles, such as, for example, saline. Any medium may be used which allows for successful delivery of the nucleic acid. One skilled in the art would readily comprehend the multitude of pharmaceutically acceptable media that may be used in the present invention. Suitable pharmaceutical carriers are described in *Remington's Pharmaceutical Sciences*, A. Osol, a standard reference text in this field, which is incorporated herein by reference.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Compositions for oral administration include powders or granules, suspensions or solutions in water or non-aqueous media, capsules, sachets or tablets. Thickeners, flavoring agents, diluents, emulsifiers, dispersing aids or binders may be desirable. Compositions for parenteral, intravenous, intrathecal or intraventricular administration may include sterile aqueous solutions which may also contain buffers, diluents and other suitable additives and are preferably sterile and pyrogen free. Pharmaceutical compositions which are suitable for intravenous administration according to the invention are sterile and pyrogen free.

The pharmaceutical compositions of the present invention may be administered by any means that enables the active agent to reach the agent's site of action in the body of a mammal. The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral Parenteral administration includes intravenous drip, subcutaneous, intraperitoneal or intramuscular injection, pulmonary administration, e.g., by inhalation or insufflation, or intrathecal or intraventricular administration.

Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Formulation of therapeutic compositions and their subsequent administration is believed to be within the skill of those in the art.

Hybridomas which produce antibodies that bind to hVIP, and the antibodies themselves, are useful in the isolation and purification of hVIP and protein complexes that include hVIP. In addition, antibodies are specific inhibitors of hVIP activity. Antibodies which specifically bind to hVIP may be used to purify the protein from natural sources using well known techniques and readily available starting materials. Such antibodies may also be used to purify the protein from material present when producing the protein by recombinant DNA methodology.

As used herein, the term "antibody" is meant to refer to complete, intact antibodies, and Fab fragments and F(ab)$_2$ fragments thereof. Complete, intact antibodies include monoclonal antibodies such as murine monoclonal antibodies, chimeric antibodies and humanized antibodies. In some embodiments, the antibodies specifically bind to an epitope of SEQ ID NO:2. Antibodies that bind to an epitope is useful to isolate and purify that protein from both natural sources or recombinant expression systems using well known techniques such as affinity chromatography. Such antibodies are useful to detect the presence of such protein in a sample and to determine if cells are expressing the protein.

The production of antibodies and the protein structures of complete, intact antibodies, Fab fragments and F(ab)$_2$ fragments and the organization of the genetic sequences that encode such molecules are well known and are described, for example, in Harlow, E. and D. Lane (1988) *ANTIBODIES: A Laboratory Manual,* Cold Spring Harbor Laboratory, Cold Spring Harbor, N.Y. which is incorporated herein by reference. Briefly, for example, hVIP, or an immunogenic fragment thereof, is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to hVIP, the hybridoma which produces them is cultured to produce a continuous supply of antibodies.

The present invention relates to fragments of Vpr which interact with hVIP to prevent or inhibit G2/M transition by cells. Vpr is known to have the ability to arrest the cell cycle. The discovery of the cellular protein hVIP which Vpr interacts with in connection with the arrest of the cell cycle cells provides for the targeting of hVIP by Vpr and fragments of Vpr which maintain their ability to arrest the cell cycle. According to some embodiments, the fragment also retains its ability to localize in the nucleus.

The amino acid sequence of Vpr is disclosed in U.S. Ser. No. 08/167,608 filed Dec. 15, 1993, which is incorporated herein by reference. According to the invention, pharmaceutical compositions are provided which comprise fragments of Vpr which interact with hVIP to prevent or inhibit G2/M transition by cells. Data from Vpr protein mapping experiments to identify regions that specifically interact with and arrest cell cycle arrest are described in Provisional Application 60/055,754 filed Aug. 14, 1997, which is incorporated herein by reference.

Fragments of Vpr can be identified which interact with hVIP to prevent or inhibit G2/M transition by cells. Some embodiments of the invention are fragments of Vpr which comprise at least three amino acids and which bind to hVIP. In some embodiments, fragments of Vpr are less than 50 amino acids. In some embodiments, fragments of Vpr are less than 25 amino acids. In some embodiments, fragments of Vpr are less than 20 amino acids. In some embodiments, fragments of Vpr are less than 15 amino acids. In some embodiments, fragments of Vpr are less than 13 amino acids. In some embodiments, fragments of Vpr are less than 10 amino acids. In some embodiments, fragments of Vpr are less than 8 amino acids. In some embodiments, fragments of Vpr are less than 5 amino acids.

Some embodiments of the invention are peptides which comprise fragments of Vpr which comprise at least three amino acids and which bind to hVIP. In some embodiments, the peptides are less then 25 amino acids. In some embodiments, the peptides comprise fragments of Vpr that are less than 25 amino acids. In some embodiments, the peptides comprise fragments of Vpr that are less than 20 amino acids. In some embodiments, the peptides comprise fragments of Vpr that are less than 15 amino acids. In some embodiments, the peptides comprise fragments of Vpr that are less than 10 amino acids. In some embodiments, the peptides comprise fragments of Vpr that are less than 8 amino acids. In some embodiments, the peptides comprise fragments of Vpr that are less than 5 amino acids. In some embodiments, the peptides comprise fragments of Vpr that are less than 4 amino acids.

In some embodiments, the compounds of the present invention are: 20 amino acids or less; consist of or comprise a fragment of Vpr that is at least 3 amino acids and that binds to hVIP; and are useful to arrest the cell cycle. The peptides of the invention comprise amino acid sequences that consist of 20 amino acids or less, preferably 10–15 amino acids or less. As used herein, the term "compound" refers to molecules which include peptides and non-peptides including, but not limited to molecules which comprise amino acid residues joined by at least some non-peptidyl bonds. As used herein, the term "peptide" refers to polypeptides formed from amino acid subunits joined by native peptide bonds. The term "amino acid" is meant to refer to naturally occurring amino acid moieties and to moieties which have portions similar to naturally occurring peptides but which have non-naturally occurring portions. Thus, peptides may have altered amino acids or linkages. Peptides may also comprise other modifications consistent with the spirit of this invention. Such peptides are best described as being functionally interchangeable yet structurally distinct from natural peptides. As used herein, the terms "compounds" and "peptides" are used interchangeably.

Conservative substitutions of amino acid sequences of vpr fragments are contemplated. As used herein, the term "conservative substitutions" is meant to refer to amino acid substitutions of Vpr residues with other residues which share similar structural and/or charge features. Those having ordinary skill in the art can readily design vpr fragments with conservative substitutions for amino acids based upon well known conservative groups.

Peptides of some embodiments of the present invention may be from at least about 3 to up to about 20 amino acids in length. In some embodiments of the present invention, peptides of the present invention are from about 5 to about 15 amino acids in length. In preferred embodiments of the present invention peptides of the present invention are 4, 5, 6, 7, 8, 9, 10, 11, 12, 13, 14 15, 16, 17, 18 or 19 amino acids in length. It is preferred that peptides are as small as possible.

In peptides of the invention, at least 3 amino acids of the peptide is a Vpr fragment. It is preferred that the Vpr derived portion makes up at least 10% of the amino acid sequence of the peptide. In some embodiments, it is preferred that greater than about 20–25% of the amino acid sequence of the peptides of the present invention are Vpr derived, more preferably 30–40% and more preferably greater than 50%. In some embodiments, the proportion of amino acid sequence of the peptides of the present invention that are Vpr derived approaches about 60% or about 75% or more.

Synthesized peptides of the invention may be circularized in order to mimic the geometry of those portions as they occur in vpr. Circularization may be facilitated by disulfide bridges between cysteine residues. Cysteine residues may be included in positions on the peptide which flank the portions of the peptide which are derived from vpr. Cysteine residues within the portion of a peptide derived from vpr may be deleted and/or conservatively substituted to eliminate the formation of disulfide bridges involving such residues. Alternatively, other means of circularizing peptides are also well known. The peptides may be circularized by means of covalent bonds, such as amide bonds, between amino acid residues of the peptide such as those at or near the amino and carboxy termini.

In some embodiments of the invention, peptides consist of 15 amino acid residues or less and are circularized or otherwise conformationally restricted by disulfide bonds arising from N- and C-terminal cysteines.

The peptides of the present invention may be prepared by any of the following known techniques. Conveniently, the peptides may be prepared using the solid-phase synthetic technique initially described by Merrifield, in *J. Am. Chem. Soc.* 15:2149–2154 (1963) which is incorporated herein by reference. Other peptide synthesis techniques may be found, for example, in M. Bodanszky et al., (1976) *Peptide Synthesis,* John Wiley & Sons, 2d Ed. which is incorporated herein by reference; Kent and Clark-Lewis in *Synthetic Peptides in Biology and Medicine,* p. 295–358, eds. Alitalo, K., et al. Science Publishers, (Amsterdam, 1985) which is incorporated herein by reference; as well as other reference works known to those skilled in the art. A summary of peptide synthesis techniques may be found in J. Stuart and J. D. Young, *Solid Phase Peptide Synthelia,* Pierce Chemical Company, Rockford, Ill. (1984) which is incorporated herein by reference. The synthesis of peptides by solution methods may also be used, as described in *The Proteins,* Vol. II, 3d Ed., p. 105–237, Neurath, H. et al., Eds., Academic Press, New York, N.Y. (1976) which is incorporated herein by reference. Appropriate protective groups for use in such syntheses will be found in the above texts, as well as in J. F. W. McOmie, *Protective Groups in Organic Chemistry,* Plenum Press, New York, N.Y. (1973) which is incorporated herein by reference.

In general, these synthetic methods involve the sequential addition of one or more amino acid residues or suitable protected amino acid residues to a growing peptide chain. Normally, either the amino or carboxyl group of the first amino acid residue is protected by a suitable, selectively-removable protecting group. A different, selectively removable protecting group is utilized for amino acids containing a reactive side group, such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptide of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

The peptides can be tested following the methods herein to determine whether they bind to hVIP and arrest the cell cycle. Those peptides which bind to hVIP and arrest the cell cycle are useful as in the treatment of conditions, diseases and disorders characterized by undesirable cell proliferation such as cancer.

The present invention provides pharmaceutical compositions that comprise the compounds of the invention and pharmaceutically acceptable carriers or diluents.

The pharmaceutical composition of the present invention may be formulated by one having ordinary skill in the art with compositions selected depending upon the chosen mode of administration. Suitable pharmaceutical carriers are described in *Remington's Pharmaceutical Sciences,* A.

Osol, a standard reference text in this field. In carrying out methods of the present invention, peptides of the present invention can be used alone or in combination with other diagnostic, therapeutic or additional agents. Such additional agents include excipients such as flavoring, coloring, stabilizing agents, thickening materials, osmotic agents and antibacterial agents. Such agents may enhance the peptide's use in vitro, the stability of the composition during storage, or other properties important to achieving optimal effectiveness.

Pharmaceutical compositions which are suitable for intravenous administration according to the invention are sterile and pyrogen free. Pharmaceutical formulation described above may be prepared according to the invention using fragments of Vpr which interact interact with hVIP to prevent or inhibit G2/M transtion by cells as starting materials.

For parenteral administration, the peptides of the invention can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions according to the present invention may be administered as a single dose or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The pharmaceutical compositions of the present invention may be administered by any means that enables the active agent to reach the targeted cells. Because peptides are subject to being digested when administered orally, parenteral administration, i.e., intravenous, subcutaneous, transdermal, intramuscular, would ordinarily be used to optimize absorption. Intravenous administration may be accomplished with the aid of an infusion pump. The pharmaceutical compositions of the present invention may be formulated as an emulsion. Alternatively, they may be formulated as aerosol medicaments for intranasal or inhalation administration. In some cases, topical administration may be desirable.

The dosage administered varies depending upon factors such as: pharmacodynamic characteristics; its mode and route of administration; age, health, and weight of the recipient; nature and extent of symptoms; kind of concurrent treatment; and frequency of treatment. Usually, the dosage of peptide can be about 1 to 3000 milligrams per 50 kilograms of body weight; preferably 10 to 1000 milligrams per 50 kilograms of body weight; more preferably 25 to 800 milligrams per 50 kilograms of body weight. Ordinarily 8 to 800 milligrams are administered to an individual per day in divided doses 1 to 6 times a day or in sustained release form is effective to obtain desired results.

Depending upon the disease or disorder to be treated, the pharmaceutical compositions of the present invention may be formulated and administered to most effectively. Modes of administration will be apparent to one skilled in the art in view of the present disclosure.

The present invention relates to isolated nucleic acid molecules that encode fragments of Vpr which interact with hVIP to prevent or inhibit G2/M transtion by cells. DNA molecules encoding the fragments can be isolated or synthesized and cloned into vectors such as expression vectors useful for production of the protein ore as gene therpay vectors which can be delivered as pharmaceutical agents in gene therapy protocols. In protein production applications, using standard recombinant DNA methodology and starting materials such as those described above, the expression vectors are inserted into an appropriate host cell which is cultured and from which the protein is isolated. In gene therpay applications, the DNA is inserted into a vector selected to introduce the DNA into the cell that is intended to be arrested.

The fragments of Vpr which interact interact with hVIP to prevent or inhibit G2/M transtion by cells or the DNA molecules that encode them may be used in methods of inhibiting cells from transitioning from M to G2. The methods comprise the steps of contacting cells with a fragments of Vpr which interact with hVIP to prevent or inhibit G2/M transtion by cells or a nucleotide sequence that encodes fragments of Vpr which interact with hVIP to prevent or inhibit G2/M transtion by cells which is expressed by the cells. Such methods oare useful totreat patients that have diseases characteirzed by cells whose proliferation is undesirable such as hyperproliferative diseases and some autoimmune diseases. Division of hyperproliferating cells or prolieferating cells associated with an undesirable immune response may be arrested or inhibited thus reducing the number of such undesirable cells and therby producing a therapeutic benefit to the patient.

Another aspect of the present invention relates to methods of identifying anti-HIV compounds. Accoridng to this aspect, the hVIP or a fragment of hVIP known to interact with Vpr is contacted with Vpr or a fragment of Vpr which interacts with hVIP to prevent or inhibit G2/M transtion by cells in the presence of a test compound. The affininty of the hVip or fragment thereof to the Vpr or fragment thereof is measured and compared to the affininty of the hVip or fragment thereof to the Vpr or fragment thereof in the absence of a test compound. Compounds which can disrupt the binding of Vpr to hVIP may be useful as anti-HIV compounds. An example of a positive control in this drug screen assay would be anti-hVIP antibodies which compettititively bind to hVIP with respect to Vpr. Another example of a positive control in this drug screen assay would be anti-Vpr antibodies which competititively bind to Vpr with respect to hVIP. Such antibodies are useful as known compounds that disrupt the hVIP/Vpr interaction. Known quanties of Vpr and hVIP may be combined under conditions suitable for binding. In some embodiments of the invention, the preferred concentration of test compound is between 1 $\mu$M and 500 $\mu$M. A preferred concentration is 10 $\mu$M to 100 $\mu$M. In some preferred embodiments, it is desirable to use a series of dilutions of test compounds.

The present invention is further illustrated by the following examples, which are not intended to be limiting in any way.

EXAMPLES

Example 1

Cloning of hVIP

Yeast two-hybrid screening and 5' RACE were used to isolate a full length 1.35 kb cDNA containing a 1023 bp open reading frame. The entire cDNA sequence of hVIP is set forth in SEQ ID NO:1 and the amino acid sequence encoded thereby is set forth in SEQ ID NO:2. SEQ ID NO:3 contains an alternative cDNA sequence which includes untranslated sequences. The amino acid sequence encoded by SEQ ID NO:3 is set forth in SEQ ID NO:4. The complete hVIP amino acid sequence with the data bank did not produce significant homology with any known sequences. Nine dipeptide leucine-isoleucine motifs and several Leu-Isoleu repeats were noted in the amino acid sequence of hVIP. In general, such Leu-Isoleu repeats are believed to mediate protein-protein interactions. Suzuki, et al., *Proc. Natl. Acad. Sci. USA*, 1990, 92, 3794–3798; and Draper, et al., *Mol. Cell. Biol.*, 1994, 14, 4522–4531. The hVIP cDNA is approximately 1.35 kb which corresponds to the size detected in northern blots containing poly(A)$^+$ from several human organs and RNA from CEM, PBMCs, and human rhabdomyosarcoma cell line (RD) using hVIP cDNA as a probe (see, FIG. 1B). This diverse expression pattern suggests a role for hVIP in the biology of divergent cell lines not merely in cellular targets for HIV.

Example 2

Preparation of hVIP Protein

Figure 1C:
FIG. 1C shows hVIP expression detected by an immunoprecipitation assay. hVIP cDNA was fused in-frame with an Anti-Xpress epitope tagged with a 6His mammalian expression vector pcDNA3.His (Invitrogen).
Figure 1D:
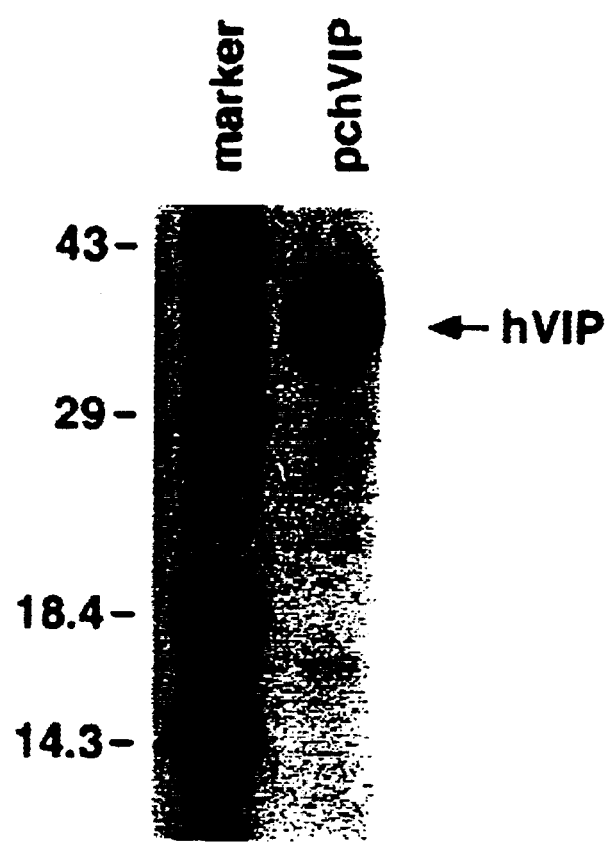
FIG. 1A shows that hVIP cDNA contains a single long ORF that is translated from the first in-frame initiation codon. Dipeptide leucine and iosleucine motifs and repeats are underlined.
Figure 2:
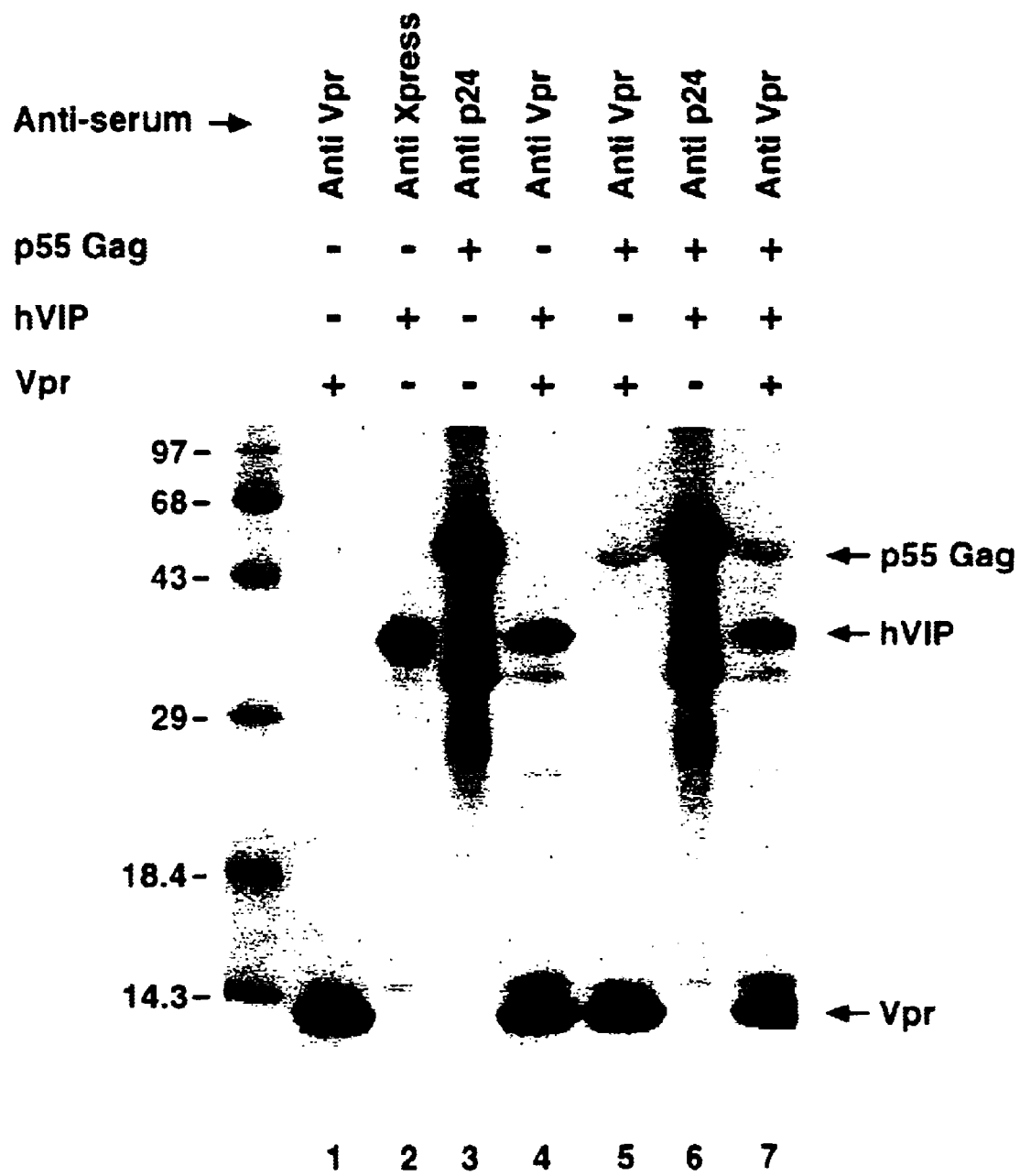
FIG. 2 shows interaction of hVIP with HIV-1 Vpr in vitro by a coimmunoprecipitation assay. The relative mobility of the marker protein is indicated at the left by size in kilodaltons.
Figures 3A, 3B, 3C, 3D, 3E, 3F, 3G, 3H:
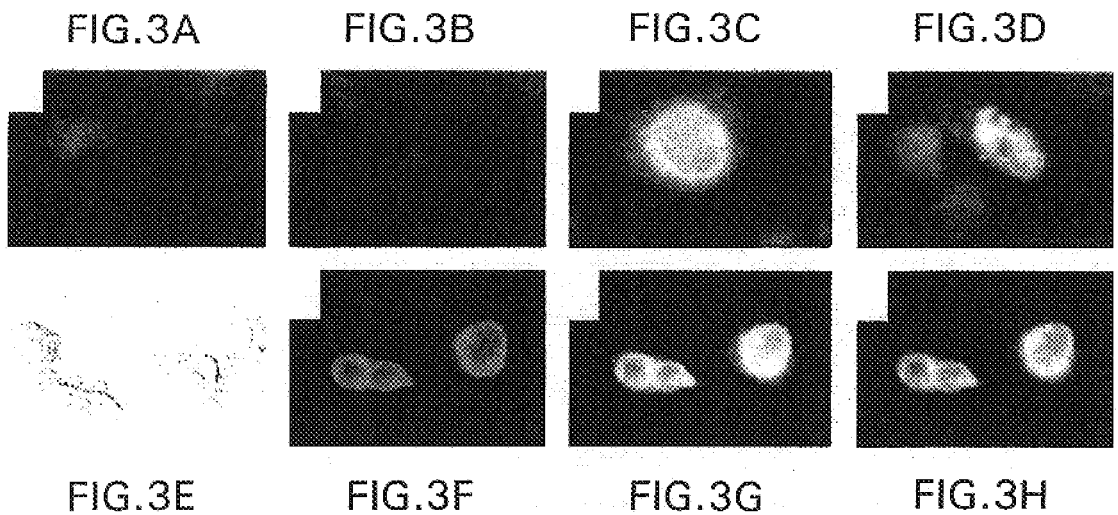
FIG. 3 shows subcellular distribution and colocalization of hVIP and Vpr by indirect immunofluorescence assay. Panels a–d show HeLa cells were transfected with either hVIP or HIV-1 Vpr expression vectors, fixed for immunofluorescence as described previously (Mahalingam, et al., *Virology*, 1995, 212, 331–339), probed with anti-Vpr (panels a and c) and Anti-Xpress antibody (panels b and d), and stained with Fluorescein-conjugated goat anti-rabbit for Vpr or goat anti-mouse secondary antibody for hVIP. Panels a and b were vector transfected; panel c, Vpr and panel d, hVIP. Panels e–h show colocalization of hVIP and Vpr. Panel e shows a phase contrast field; panel f shows rhodamine specific Vpr fluorescence; panel g shows fluorescein specific hVIP fluorescence; and panel h shows double exposure in which the colorization of rhodamine and fluorescein appears yellow.

The biology of hVIP was investigated by fusing full length hVIP cDNA inframe with an Anti-Xpress epitope tagged 6His mammalian expression vector, pcDNA3.His. hVIP cDNA expresses a polypeptide of relative molecular mass of 39,000 (Mr 39 k) which was detected by immunoprecipitation using monoclonal Anti-Xpress epitope antibody (see, FIG. 1C). HeLa cells were transfected with hVIP expression vectors then labeled with $^{35}$S protein labeling mix (NEN) and hVIP was immunoprecipitated using Anti-Xpress antibody and analyzed on SDS15%-PAGE. In an effort to demonstrate the existence of a physical interaction between Vpr and hVIP as suggested by the yeast two hybrid assay, we looked to see if Vpr would form a complex with hVIP in vitro. For this purpose, we mixed equal amounts of $^{35}$S labeled in vitro translated hVIP with $^{35}$S labeled Vpr and/or HIV-1 p55gag precursor polyprotein (as control). The relevant mixtures were incubated with their respective antiserum and their interaction was analyzed by coimmunoprecipitation. FIG. 2 shows that both Vpr and hVIP were coimmunoprecipated by anti-Vpr antiserum. Equal amounts of $^{35}$S radiolabeled in vitro translated hVIP was incubated with HIV-1 Vpr and p55gag precursor polyprotein on ice with binding buffer for 30 minutes. The protein complexes were immunoprecipitated with either anti-Vpr, Anti-Express or anti-p24 antibodies then subjected to SDS 15%-PAGE. The hVIP protein did not coimmunoprecipitate with p55gag by anti-p24 antibody, but did coimmunoprecipitate specifically with Vpr by anti-Vpr antiserum. Polyclonal antiserum against p55gag did not immunoprecipitate hVIP. Interestingly, anti-Vpr antiserum immunoprecipitated by p55gag and hVIP suggesting a lack of competition and distinct binding sites on Vpr for both ligands. These data demonstrate that the specific interaction of hVIP and Vpr can be recapitulated in vitro and that the interaction is direct.

Example 3

Localization of hVIP hVIP localized to the nucleus with a punctate staining pattern and Vpr localized to the periphery of the nucleus. HeLa cells were cotransfected with hVIP and HIV-1 Vpr expression vectors then fixed for immunofluorescence.

Fixed cells were probed with anti-rabbit polyclonal primary antibody followed by staining with rhodamine-conjugated goat anti-rabbit secondary antibody for Vpr. The cells were probed with monoclonal Anti-Xpress antibody followed by Fluorescein-conjugated goat anti-mouse secondary antibody for hVIP.

Figure 4B:
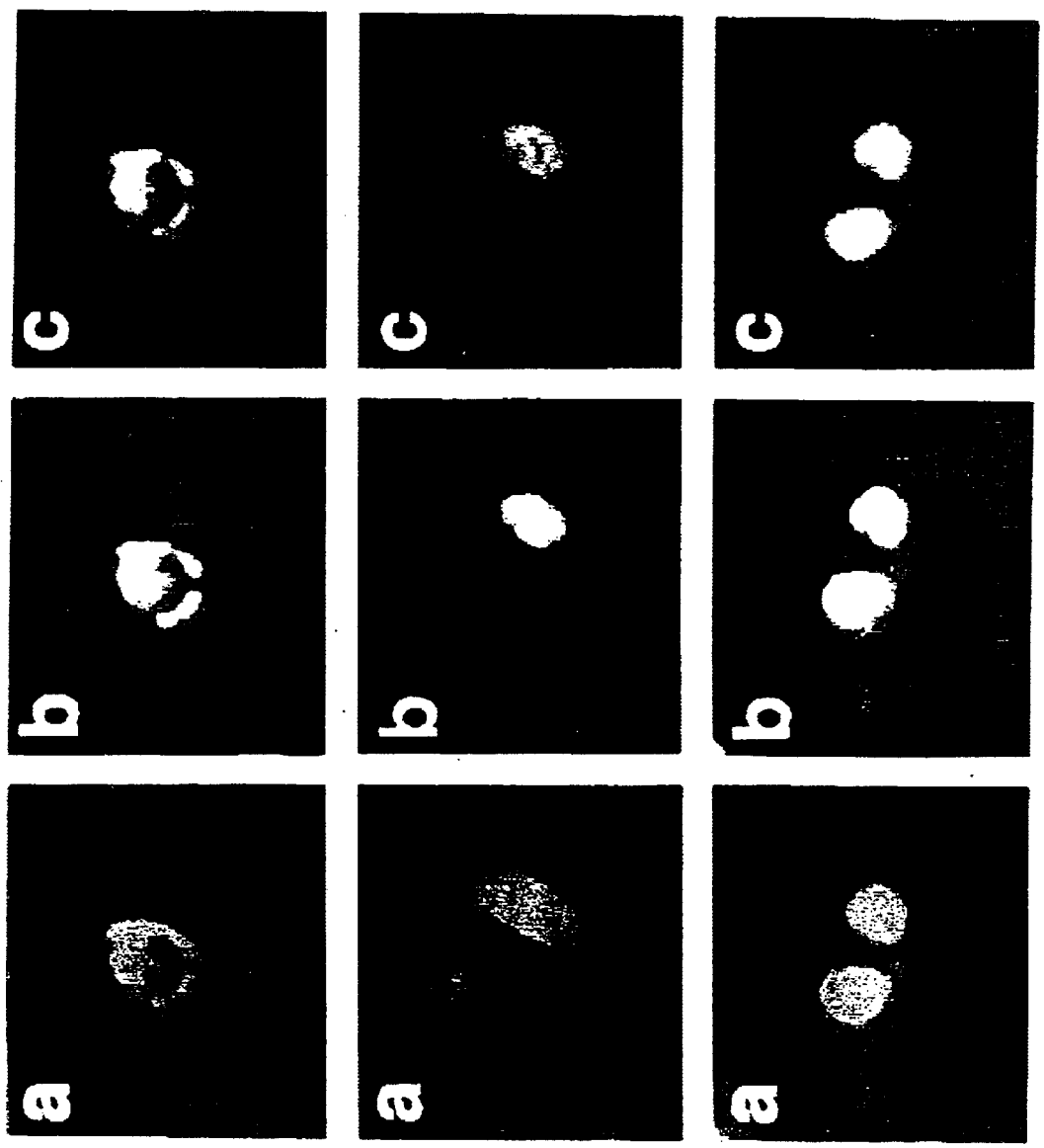
FIG. 4B shows subcellular distribution of hVIP with different Vpr mutants were assayed by indirect immunofluorescence.
Figure 5A:
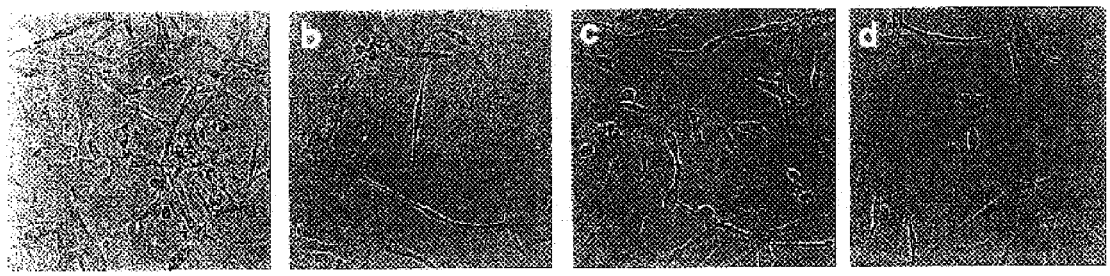
FIGS. 5A and 5B show antisense hVIP inhibits cellular proliferation
Figures 1, 5B:
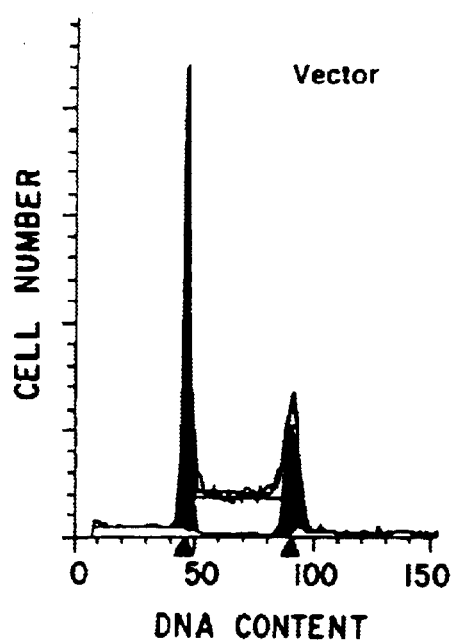
Figures 2, 5B:
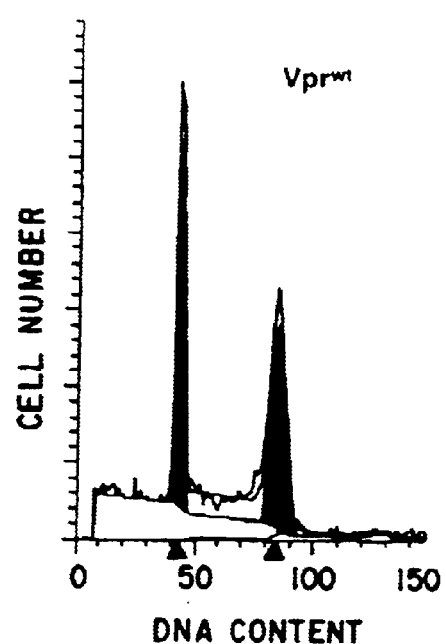
Figures 3, 5B:
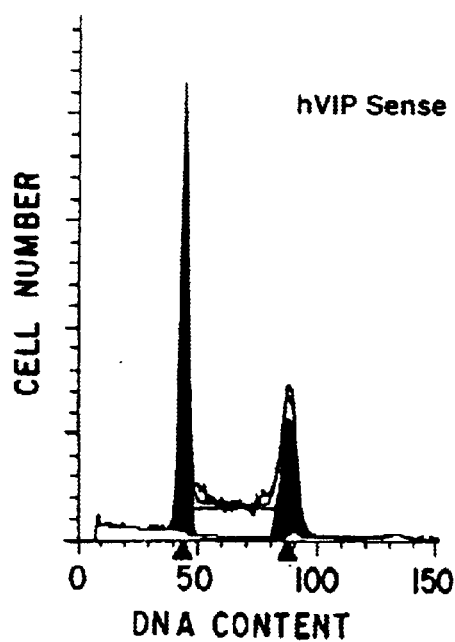
Figures 4, 5B:
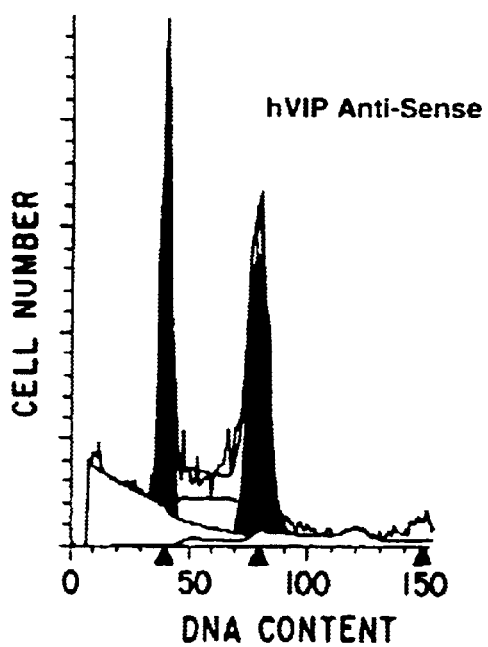

Virtually all of the expressed hVIP localized to the nucleus forming a punctuate staining pattern (see, FIG. 3, panel d). In contrast, Vpr is localized to the periphery of the nucleus (see, FIG. 3, panel c). We next looked to see whether hVIP and Vpr staining would colocalize to the nucleus of cotransfected cells. Two color immunostaining with rabbit polyclonal Vpr antibody and Anti-Xpress epitope monoclonal antibody was performed. These assays revealed that the coexpression of Vpr and hVIP strongly altered the distribution of hVIP from a punctate nuclear to a perinuclear pattern (see, FIG. 3, panel g). Significant colocalization of hVIP and Vpr was observed in the periphery of the nucleus in the presence of Vpr (see, FIG. 3, panel f). The alteration in subcellular localization of hVIP induced by coexpression with wild-type Vpr was specific in that it was not altered by cotransfection with an expression vector encoding either mutant Vpr molecules (see, FIG. 4B) or HIV-1 p55gag precursor polyprotein (data not shown). This suggests that HIV-1 Vpr interacts with hVIP and alters the subcellular distribution of hVIP and supports the assertion that hVIP and Vpr physically interact in vivo.

Example 4

Interaction of hVIP with Vpr

To identify the domains of Vpr required for its interaction with hVIP and cell cycle arrest, we generated different mutant Vpr molecules by overlap PCR as described previously. Mahalingam, et al., *Virology*, 1995, 212, 331–339. The correlation between the localization of Vpr mutants with hVIP and cell cycle arrest was assessed. HeLa cells were cotransfected with different Vpr mutants (A30L, αL-A. A59P, L67S, H71C, G75A, and C76S) and the hVIP expression plasmids and studied their subcellular localization. The transfected cells were fixed and stained as described above and visualized with fluorescence and rhodamine wavelength filters to detect expression and the cell cycle arrest activity of Vpr mutants were determined by flow cytometric analysis FIGS. 4A and 4B show that Vpr mutants A30L, A59P, L67S, H71C, G75A, and C76S do not alter the subcellular distribution of hVIP (see, FIGS. 4A and 4B) nor inhibit cellular proliferation (see, FIG. 4A). hVIP localized to the cytoplasm when coexpressed with Vpr mutant α L-A. Interestingly, this mutant maintains the cell cycle arrest function of wild-type Vpr and prevents the nuclear import of hVIP (see, FIG. 4B). These data clearly demonstrate that the amino acid residues in the carboxy-terminus are essential for the interaction between Vpr and hVIP and for altering the subcellular localization of hVIP in cell cycle arrest.

Example 5 hVIP and Cell Cycle

In order to confirm that hVIP is essential for the transition from G2 to M phase of cell division, an antisense hVIP and control expression vector pBabepuro (a vector which confers puromycin resistance) were constructed. The antisense hVIP contained a full length hVIP nucleotide sequences oriented for production of antisense molecules. RD cells were transfected with Vpr, hVIP sense, and antisense expression vectors and were selected with puromycin. FIGS. 5A and 5B reveal a significant reduction in the number of cells in Vpr and hVIP antisense transfected plates and shows that cells expressing Vpr and antisense hVIP are blocked at the G2/M phase of the cell cycle (see, FIG. 5B). Similar results were obtained in several diverse human tumor cell lines including HeLa, MCF-7, and SW480. In cycling cells, the transition of G2 to M is regulated by cyclin-dependent kinase p34$^{cdc1}$ and cyclin B complex. Norbury, et al., *Biochem. Biophys.* Acta, 1989, 989, 85–89; and Murray, *Nature,* 1992, 359, 599–604. Late in G2, p34$^{cdc}$ is dephosphorylated at amino acid residues Thr14 and Thr15. This activates the complex which then phosphorylates several cellular substrates involved in the intricate events of M phase. hVIP is an essential cellular factor which is required for the initiation of M phase. Further studies will be required to determine whether hVIP interacts directly or indirectly with either cyclin B or p34$^{cdc}$ or other members of the cell cycle cascade.

Example 6

Yeast Two Hybrid Interaction Assay

Full length HIV-1 Vpr was fused in-frame with GAL-4 DNA binding domain yeast expression vector pGBT9 (Clontech). The two hybrid screen was performed using a GAL4 activation domain tagged PBL cDNA library (Clontech) and GAL4 Vpr construct used as bait. After four days of selection on culture plates, double transformants were transferred onto filter paper (VWR) and analyzed for β-gal expression according to the manufacturer's protocol (Clontech). Three clones were recovered and all contained the Carboxyl-terminal portion of hVIP starting at amino acid 31. 5'RACE was performed to isolate the 5" end of the hVIP gene fragment using total RNA from CEM and HeLa cells according to the instruction manual (Boehringer Mannheim). All the molecular clones were sequenced using the dideoxy chain termination method (United States Biochemical) and the automatic sequencing method using Amplitag (Perkin Elmer).

Example 7

RNA and Protein Expression

Multitissue northern blot was purchased from Clontech and the total RNA was isolated from CEM, RD, and PBMCs. The blots were probed with a random-primed $^{32}$P dCTP labeled probe prepared from an internal 1009 bp EcoRI hVIP cDNA fragment. A T7 RNA polymerase (vFT7-3) based expression system was used to assay the expression of hVIP in tissue culture cells. Mahalingam, et al. *Virology,* 1995, 212, 331–339; and Fuerst, et al., *Mol. Cell. Biol.,* 1987, 7, 2538–2544. hVIP cDNA was fused in-frame with an Anti-Xpress antibody epitope tagged 6His mammalian expression vector pCDNA3.His (Invitrogen) and used for expression studies. HeLa cells were infected with vFT7-3 and transfected with the hVIP expression plasmid using Lipofectin (GIBCO-BRL). After overnight transfection, the cells were labeled with $^{35}$S Express protein labeling mix (NEN) for two hours, hVIP was immunoprecipitated using monoclonal Anti-Express antibody, and subjected to SDS 15%-PAGE.

Example 8

Coimmunoprecipitation Assay

Equal levels of in vitro translated hVIP, HIV-1 Vpr, and p55 Gag precursor polyprotein were mixed and incubated for 30 minutes at 4° C. in a binding buffer containing 25 mM HEPES (pH7.9), 150 mM KCl, 0.1% NP40, 5% glycerol, 0.5 mM dithiothreitol, 0.4 mM phenyl methyl sulphonyl fluoride. Respective antibodies were added to each tube with 150 ml binding buffer and incubated for 90 minutes at 4° C. Protein A sepharose (5 mg/tube) was added to all the tubes which were then incubated at 4° C. for 90 minutes in a rotating shaker. The beads were then washed three times with the binding buffer. The immunoprecipitated protein complexes were eluted from the sepharose beads and subjected to SDS15%-PAGE. The gel was processed for fluorography as described previously. Mahalingam, et al., *DNA Cell Biol.*, 1997, 16, 137–153.

Example 9

Cell Cycle Analysis

HeLa or RD cells were cotransfected with either wild type or mutant Vpr and hVIP sense, or antisense expression vectors with the pBabepuro (a vector that expresses puromycin resistance). Two days later, puromycin was added at a concentration of 2 μg/ml to eliminate the untransfected cells. The transfected cells were stained with propidium iodide five to seven days post transfection for analysis of DNA content by flow cytometry.

Example 10

Indirect Immunofluorescence

HeLa cells were transfected with either Vpr or hVIP expression vectors along or in combination. Immunofluorescence staining of fixed HeLa cells with the indicated primary antibody followed by FITC (Boehringer Mannheim) or rhodamine (Sigma) conjugated secondary antibody was performed as described previously. Mahalingam, et al., *Virology*, 1995, 212, 331–339. Indirect immunofluorescence was carried out with rabbit anti-Vpr (1:50) or mouse Anti-Xpress monoclonal (1:100) (Invitrogen) alone or in combination This was followed by staining with either rhodamine conjugated goat anti-rabbit IgG(1:75) or FITC-conjugated goat anti-mouse IgG(1:100) or both.

What is claimed is:

1. A method of identifying an anti-HIV compound comprising the steps of:
   contacting human Vpr Interacting Protein (hVIP), or a fragment thereof known to interact with Vpr, with Vpr, or a fragment thereof known to interact with hVIP in the presence of a test compound; and
   comparing the affinity of said hVIP or fragment thereof to said Vpr or fragment thereof in the presence of said test compound with the affinity of said hVIP or fragment thereof to said Vpr or fragment thereof in the absence of said test compound;
   wherein a decrease in said affinity in the presence of said test compound indicates that said test compound is an anti-HIV compound.

2. The method of claim 2 wherein said test compound is an antibody.

3. The method of claim 2 wherein said antibody is a monoclonal antibody.

4. The method of claim 2 wherein said antibody is an anti-hVIP antibody.

5. The method of claim 1 wherein said antibody is an anti-Vpr antibody.

6. The method of claim 1 wherein said test compound is an oligonucleotide.

7. The method of claim 6 wherein said oligonucleotide comprises a nucleotide sequence complementary to a nucleotide sequence of at least 10 nucleotides of SEQ ID NO:1.

8. The method of claim 6 wherein said oligonucleotide consists of a nucleotide sequence complementary to a nucleotide sequence of 10–150 nucleotides of SEQ ID NO:1.

9. The method of claim 6 wherein said oligonucleotide consists of a nucleotide sequence complementary to a nucleotide sequence of 18–28 nucleotides of SEQ ID NO:1.

10. The method of claim 1 wherein the concentration of said test compound is between 1 $\mu$M and 500 $\mu$M.

11. The method of claim 10 wherein said concentration is between 10 $\mu$M and 100 $\mu$M.

12. The method of claim 1 wherein said human Vpr Interacting Protein (hVIP), or a fragment thereof known to interact with Vpr, is contacted with Vpr, or a fragment thereof known to interact with hVIP in the presence of a series of dilutions of test compounds.

13. The method of claim 1 wherein said hVIP comprises SEQ ID NO:2.

14. The method of claim 1 wherein said Vpr fragment comprises less than 25 amino acids.

15. The method of claim 14 wherein said Vpr fragment comprises less than 20 amino acids.

16. The method of claim 14 wherein said Vpr fragment comprises less than 15 amino acids.

17. The method of claim 14 wherein said Vpr fragment comprises less than 10 amino acids.

18. The method of claim 14 wherein said Vpr fragment comprises less than 8 amino acids.

19. The method of claim 14 wherein said Vpr fragment comprises less than 5 amino acids.

20. A transgenic non-human mammal comprising a recombinant expression vector that comprises a nucleic acid sequence that encodes hVIP.

21. The transgenic non-human mammal of claim 20 wherein said hVIP comprises SEQ ID NO:2.

22. The transgenic non-human mammal of claim 20 wherein said nucleic acid sequence that encodes hVIP is operably linked to a mammary cell-specific promoter.

23. The transgenic non-human mammal of claim 22 wherein said hVIP is only expressed in mammary cells.

24. The tranagenic non-human mammal of claim 23 wherein said hVIP is recovered from the mammal's milk.

25. The transgenic non-human mammal of claim 20 wherein said nucleic acid sequence that encodes hVIP comprises SEQ ID NO:1.

26. The non-human mammal of claim 20 wherein said mammal is a goat.

27. The transgenic non-human mammal of claim 20 wherein said mammal is a rodent.

28. The transgenic non-human mammal of claim 27 wherein said rodent is a rat or mouse.

* * * * *

SEQUENCE LISTING

<160> NUMBER OF SEQ ID NOS: 4

<210> SEQ ID NO 1
<211> LENGTH: 1260
<212> TYPE: DNA
<213> ORGANISM: Homo sapiens
<220> FEATURE:
<221> NAME/KEY: CDS
<222> LOCATION: (1)..(1026)

<400> SEQUENCE: 1

```
atg cat gct cga gcg gcc gcc agt gtg atg gat atc tgc aga att cgg      48
Met His Ala Arg Ala Ala Ala Ser Val Met Asp Ile Cys Arg Ile Arg
  1               5                  10                  15 ctt gac cac gcg gta tcg atg tcg act ttt ttt ttt ttt tta agc agc      96
Leu Asp His Ala Val Ser Met Ser Thr Phe Phe Phe Phe Leu Ser Ser
             20                  25                  30 ggg atg gag gtg gat gca gca gta gtc ccc agc gtg atg gcc tgc gga    144
Gly Met Glu Val Asp Ala Ala Val Val Pro Ser Val Met Ala Cys Gly
         35                  40                  45 gtg act ggg agt gtt tcc gtc gct ctc cat ccc ctt gtc att ctc aac    192
Val Thr Gly Ser Val Ser Val Ala Leu His Pro Leu Val Ile Leu Asn
     50                  55                  60 atc tca gac cac tgg atc cgc atg cgc tcc cac cag ggg cgg cct gtg    240
Ile Ser Asp His Trp Ile Arg Met Arg Ser His Gln Gly Arg Pro Val
 65                  70                  75                  80 cag gtg att ggg gct ctg att ggc aag cag gag ggc cga aat atc gag    288
Gln Val Ile Gly Ala Leu Ile Gly Lys Gln Glu Gly Arg Asn Ile Glu
                 85                  90                  95 gtg atg aac tcc ttt gag ctg ctg tcc cac acc gtg gaa gag aag att    336
Val Met Asn Ser Phe Glu Leu Leu Ser His Thr Val Glu Glu Lys Ile
            100                 105                 110 atc att gac aag gaa tat tac acc aag gag gag cag ttt aaa cag        384
Ile Ile Asp Lys Glu Tyr Tyr Thr Lys Glu Glu Gln Phe Lys Gln
        115                 120                 125 gtg ttc aag gag ctg gag ttt ctg ggt tgg tat acc aca ggg ggg cca    432
Val Phe Lys Glu Leu Glu Phe Leu Gly Trp Tyr Thr Thr Gly Gly Pro
    130                 135                 140
```

```
cct gac ccc tcg gac atc cac gtc cat aag cag tgt tgt gag atc atc      480
Pro Asp Pro Ser Asp Ile His Val His Lys Gln Cys Cys Glu Ile Ile
145                 150                 155                 160 gag agc ccc ctc ttt ctg aag ttg aac cct atg acc aag cac aca gat      528
Glu Ser Pro Leu Phe Leu Lys Leu Asn Pro Met Thr Lys His Thr Asp
                165                 170                 175 ctt cct gtc agc gtt ttt gag tct gtc att gat ata atc aat gga gag      576
Leu Pro Val Ser Val Phe Glu Ser Val Ile Asp Ile Ile Asn Gly Glu
            180                 185                 190 gcc aca atg ctg ttt gct gag ctg acc tac act ctg gcc aca gag gaa      624
Ala Thr Met Leu Phe Ala Glu Leu Thr Tyr Thr Leu Ala Thr Glu Glu
        195                 200                 205 gcg gaa cgc att ggt gta gac cac gta gcc cga atg aca gca aca ggc      672
Ala Glu Arg Ile Gly Val Asp His Val Ala Arg Met Thr Ala Thr Gly
    210                 215                 220 agt gga gag aac tcc act gtg gct gaa cac ctg ata gca cag cac agc      720
Ser Gly Glu Asn Ser Thr Val Ala Glu His Leu Ile Ala Gln His Ser
225                 230                 235                 240 gcc atc aag atg ctg cac agc cgc gtc aag ctc atc ttg gag tac gtc      768
Ala Ile Lys Met Leu His Ser Arg Val Lys Leu Ile Leu Glu Tyr Val
                245                 250                 255 aag gcc tct gaa gcg gga gag gtc ccc ttt aat cat gag atc ctg cgg      816
Lys Ala Ser Glu Ala Gly Glu Val Pro Phe Asn His Glu Ile Leu Arg
            260                 265                 270 gag gcc tat gct ctg tgt cac tgt ctc ccg gtg ctc agc aca gac aag      864
Glu Ala Tyr Ala Leu Cys His Cys Leu Pro Val Leu Ser Thr Asp Lys
        275                 280                 285 ttc aag aca gat ttt tat gat caa tgc aac gac gtg ggg ctc atg gcc      912
Phe Lys Thr Asp Phe Tyr Asp Gln Cys Asn Asp Val Gly Leu Met Ala
    290                 295                 300 tac ctc ggc acc atc acc aaa acg tgc aac acc atg aac cag ttt gtg      960
Tyr Leu Gly Thr Ile Thr Lys Thr Cys Asn Thr Met Asn Gln Phe Val
305                 310                 315                 320 aac aag ttc aat gtc ctc tac gac cga caa ggc atc ggc agg aga atg     1008
Asn Lys Phe Asn Val Leu Tyr Asp Arg Gln Gly Ile Gly Arg Arg Met
                325                 330                 335 cgc ggg ctc ttt ttc tga tgagggtact tgaagggctg atggacaggg            1056
Arg Gly Leu Phe Phe
            340 gtcaggcaac tatcccaaag gggagggcac tacacttcct tgagagaaac cgctgtcatt   1116 aataaagggg gagcagcccc tgagctcgtg ccgaattcgg cacgagcggc acgagcggaa   1176 acgcttggtg ataccagata aaataaaata caacacaccc caatacagga tgatagttcg   1236 tgttacaaac agagatatca ttgt                                          1260

<210> SEQ ID NO 2
<211> LENGTH: 341
<212> TYPE: PRT
<213> ORGANISM: Homo sapiens

<400> SEQUENCE: 2

Met His Ala Arg Ala Ala Ser Val Met Asp Ile Cys Arg Ile Arg
1               5                   10                  15

Leu Asp His Ala Val Ser Met Ser Thr Phe Phe Phe Leu Ser Ser
                20                  25                  30

Gly Met Glu Val Asp Ala Ala Val Pro Ser Val Met Ala Cys Gly
            35                  40                  45

Val Thr Gly Ser Val Ser Val Ala Leu His Pro Leu Val Ile Leu Asn
    50                  55                  60
```

```
Ile Ser Asp His Trp Ile Arg Met Arg Ser His Gln Gly Arg Pro Val
 65                  70                  75                  80

Gln Val Ile Gly Ala Leu Ile Gly Lys Gln Glu Gly Arg Asn Ile Glu
                 85                  90                  95

Val Met Asn Ser Phe Glu Leu Leu Ser His Thr Val Glu Glu Lys Ile
            100                 105                 110

Ile Ile Asp Lys Glu Tyr Tyr Thr Lys Glu Gln Phe Lys Gln
        115                 120                 125

Val Phe Lys Glu Leu Glu Phe Leu Gly Trp Tyr Thr Thr Gly Gly Pro
130                 135                 140

Pro Asp Pro Ser Asp Ile His Val His Lys Gln Cys Cys Glu Ile Ile
145                 150                 155                 160

Glu Ser Pro Leu Phe Leu Lys Leu Asn Pro Met Thr Lys His Thr Asp
                165                 170                 175

Leu Pro Val Ser Val Phe Glu Ser Val Ile Asp Ile Ile Asn Gly Glu
            180                 185                 190

Ala Thr Met Leu Phe Ala Glu Leu Thr Tyr Thr Leu Ala Thr Glu Glu
        195                 200                 205

Ala Glu Arg Ile Gly Val Asp His Val Ala Arg Met Thr Ala Thr Gly
210                 215                 220

Ser Gly Glu Asn Ser Thr Val Ala Glu His Leu Ile Ala Gln His Ser
225                 230                 235                 240

Ala Ile Lys Met Leu His Ser Arg Val Lys Leu Ile Leu Glu Tyr Val
            245                 250                 255

Lys Ala Ser Glu Ala Gly Glu Val Pro Phe Asn His Glu Ile Leu Arg
        260                 265                 270

Glu Ala Tyr Ala Leu Cys His Cys Leu Pro Val Leu Ser Thr Asp Lys
    275                 280                 285

Phe Lys Thr Asp Phe Tyr Asp Gln Cys Asn Asp Val Gly Leu Met Ala
290                 295                 300

Tyr Leu Gly Thr Ile Thr Lys Thr Cys Asn Thr Met Asn Gln Phe Val
305                 310                 315                 320

Asn Lys Phe Asn Val Leu Tyr Asp Arg Gln Gly Ile Gly Arg Arg Met
            325                 330                 335

Arg Gly Leu Phe Phe
            340

<210> SEQ ID NO 3
<211> LENGTH: 1346
<212> TYPE: DNA
<213> ORGANISM: Homo sapiens
<220> FEATURE:
<221> NAME/KEY: CDS
<222> LOCATION: (49)..(1074)

<400> SEQUENCE: 3
cagtgaattt gtaatacgac tcactatagg gcgaattggg ccctctag atg cat gct        57
                                                    Met His Ala
                                                      1 cga gcg gcc gcc agt gtg atg gat atc tgc aga att cgg ctt gac cac        105
Arg Ala Ala Ala Ser Val Met Asp Ile Cys Arg Ile Arg Leu Asp His
    5                  10                  15 gcg gta tcg atg tcg act ttt ttt ttt tta agc agc ggg atg gag              153
Ala Val Ser Met Ser Thr Phe Phe Phe Phe Leu Ser Ser Gly Met Glu
 20                  25                  30                  35 gtg gat gca gca gta gtc ccc agc gtg atg gcc tgc gga gtg act ggg         201
```

|   |   |   |   |   |   |   |   |   |   |   |   |   |   |   |
|---|---|---|---|---|---|---|---|---|---|---|---|---|---|---|
| Val | Asp | Ala | Ala | Val | Val | Pro | Ser | Val | Met | Ala | Cys | Gly | Val | Thr | Gly |
|     |     |     | 40  |     |     |     | 45  |     |     |     | 50  |     |     |     |

```
agt gtt tcc gtc gct ctc cat ccc ctt gtc att ctc aac atc tca gac        249
Ser Val Ser Val Ala Leu His Pro Leu Val Ile Leu Asn Ile Ser Asp
             55                  60                  65 cac tgg atc cgc atg cgc tcc cac cag ggg cgg cct gtg cag gtg att        297
His Trp Ile Arg Met Arg Ser His Gln Gly Arg Pro Val Gln Val Ile
         70                  75                  80 ggg gct ctg att ggc aag cag gag ggc cga aat atc gag gtg atg aac        345
Gly Ala Leu Ile Gly Lys Gln Glu Gly Arg Asn Ile Glu Val Met Asn
         85                  90                  95 tcc ttt gag ctg ctg tcc cac acc gtg gaa gag aag att atc att gac        393
Ser Phe Glu Leu Leu Ser His Thr Val Glu Glu Lys Ile Ile Ile Asp
100             105                 110                 115 aag gaa tat tat tac acc aag gag gag cag ttt aaa cag gtg ttc aag        441
Lys Glu Tyr Tyr Tyr Thr Lys Glu Glu Gln Phe Lys Gln Val Phe Lys
                120                 125                 130 gag ctg gag ttt ctg ggt tgg tat acc aca ggg ggg cca cct gac ccc        489
Glu Leu Glu Phe Leu Gly Trp Tyr Thr Thr Gly Gly Pro Pro Asp Pro
            135                 140                 145 tcg gac atc cac gtc cat aag cag tgt tgt gag atc atc gag agc ccc        537
Ser Asp Ile His Val His Lys Gln Cys Cys Glu Ile Ile Glu Ser Pro
            150                 155                 160 ctc ttt ctg aag ttg aac cct atg acc aag cac aca gat ctt cct gtc        585
Leu Phe Leu Lys Leu Asn Pro Met Thr Lys His Thr Asp Leu Pro Val
165             170                 175 agc gtt ttt gag tct gtc att gat ata atc aat gga gag gcc aca atg        633
Ser Val Phe Glu Ser Val Ile Asp Ile Ile Asn Gly Glu Ala Thr Met
180             185                 190                 195 ctg ttt gct gag ctg acc tac act ctg gcc aca gag gaa gcg gaa cgc        681
Leu Phe Ala Glu Leu Thr Tyr Thr Leu Ala Thr Glu Glu Ala Glu Arg
            200                 205                 210 att ggt gta gac cac gta gcc cga atg aca gca aca ggc agt gga gag        729
Ile Gly Val Asp His Val Ala Arg Met Thr Ala Thr Gly Ser Gly Glu
            215                 220                 225 aac tcc act gtg gct gaa cac ctg ata gca cag cac agc gcc atc aag        777
Asn Ser Thr Val Ala Glu His Leu Ile Ala Gln His Ser Ala Ile Lys
            230                 235                 240 atg ctg cac agc cgc gtc aag ctc atc ttg gag tac gtc aag gcc tct        825
Met Leu His Ser Arg Val Lys Leu Ile Leu Glu Tyr Val Lys Ala Ser
245                 250                 255 gaa gcg gga gag gtc ccc ttt aat cat gag atc ctg cgg gag gcc tat        873
Glu Ala Gly Glu Val Pro Phe Asn His Glu Ile Leu Arg Glu Ala Tyr
260                 265                 270                 275 gct ctg tgt cac tgt ctc ccg gtg ctc agc aca gac aag ttc aag aca        921
Ala Leu Cys His Cys Leu Pro Val Leu Ser Thr Asp Lys Phe Lys Thr
            280                 285                 290 gat ttt tat gat caa tgc aac gac gtg ggg ctc atg gcc tac ctc ggc        969
Asp Phe Tyr Asp Gln Cys Asn Asp Val Gly Leu Met Ala Tyr Leu Gly
            295                 300                 305 acc atc acc aaa acg tgc aac acc atg aac cag ttt gtg aac aag ttc       1017
Thr Ile Thr Lys Thr Cys Asn Thr Met Asn Gln Phe Val Asn Lys Phe
            310                 315                 320 aat gtc ctc tac gac cga caa ggc atc ggc agg aga atg cgc ggg ctc       1065
Asn Val Leu Tyr Asp Arg Gln Gly Ile Gly Arg Arg Met Arg Gly Leu
            325                 330                 335 ttt ttc tga tgagggtact tgaagggctg atggacaggg gtcaggcaac               1114
Phe Phe
340
```

```
tatcccaaag gggagggcac tacacttcct tgagagaaac cgctgtcatt aataaaaggg   1174
gagcagcccc tgagctcgtg ccgaattcgg cacgagcggc acgagcggaa acgcttggtg   1234
ataccagata aaataaaata caacacaccc caatacagga tgatagttcg tgttacaaac   1294
agagatatca ttgtcccaat tgctttatgc cccctttaa aagggggaa tt            1346
```

<210> SEQ ID NO 4
<211> LENGTH: 341
<212> TYPE: PRT
<213> ORGANISM: Homo sapiens

<400> SEQUENCE: 4

```
Met His Ala Arg Ala Ala Ser Val Met Asp Ile Cys Arg Ile Arg
 1               5                  10                  15

Leu Asp His Ala Val Ser Met Ser Thr Phe Phe Phe Leu Ser Ser
                20                  25                  30

Gly Met Glu Val Asp Ala Ala Val Val Pro Ser Val Met Ala Cys Gly
                35                  40                  45

Val Thr Gly Ser Val Ser Val Ala Leu His Pro Leu Val Ile Leu Asn
     50                  55                  60

Ile Ser Asp His Trp Ile Arg Met Arg Ser His Gln Gly Arg Pro Val
 65                  70                  75                  80

Gln Val Ile Gly Ala Leu Ile Gly Lys Gln Glu Gly Arg Asn Ile Glu
                85                  90                  95

Val Met Asn Ser Phe Glu Leu Leu Ser His Thr Val Glu Glu Lys Ile
                100                 105                 110

Ile Ile Asp Lys Glu Tyr Tyr Tyr Thr Lys Glu Glu Gln Phe Lys Gln
                115                 120                 125

Val Phe Lys Glu Leu Glu Phe Leu Gly Trp Tyr Thr Thr Gly Gly Pro
     130                 135                 140

Pro Asp Pro Ser Asp Ile His Val His Lys Gln Cys Cys Glu Ile Ile
145                 150                 155                 160

Glu Ser Pro Leu Phe Leu Lys Leu Asn Pro Met Thr Lys His Thr Asp
                165                 170                 175

Leu Pro Val Ser Val Phe Glu Ser Val Ile Asp Ile Ile Asn Gly Glu
                180                 185                 190

Ala Thr Met Leu Phe Ala Glu Leu Thr Tyr Thr Leu Ala Thr Glu Glu
                195                 200                 205

Ala Glu Arg Ile Gly Val Asp His Val Ala Arg Met Thr Ala Thr Gly
     210                 215                 220

Ser Gly Glu Asn Ser Thr Val Ala Glu His Leu Ile Ala Gln His Ser
225                 230                 235                 240

Ala Ile Lys Met Leu His Ser Arg Val Lys Leu Ile Leu Glu Tyr Val
                245                 250                 255

Lys Ala Ser Glu Ala Gly Glu Val Pro Phe Asn His Glu Ile Leu Arg
                260                 265                 270

Glu Ala Tyr Ala Leu Cys His Cys Leu Pro Val Leu Ser Thr Asp Lys
                275                 280                 285

Phe Lys Thr Asp Phe Tyr Asp Gln Cys Asn Asp Val Gly Leu Met Ala
     290                 295                 300
```

-continued

```
Tyr Leu Gly Thr Ile Thr Lys Thr Cys Asn Thr Met Asn Gln Phe Val
305             310             315             320

Asn Lys Phe Asn Val Leu Tyr Asp Arg Gln Gly Ile Gly Arg Arg Met
            325             330             335

Arg Gly Leu Phe Phe
            340
```